US011612412B2

(12) United States Patent
Dion et al.

(10) Patent No.: US 11,612,412 B2
(45) Date of Patent: Mar. 28, 2023

(54) METHODS OF IMPLANTING A STIMULATION LEAD FOR STIMULATION OF A DORSAL ROOT GANGLION

(71) Applicant: ADVANCED NEUROMODULATION SYSTEMS, INC., Plano, TX (US)

(72) Inventors: Matthew K. Dion, Dallas, TX (US); T. J. Baggett, Murphy, TX (US)

(73) Assignee: Advanced Neuromodulation Systems, Inc., Plano, TX (US)

( * ) Notice: Subject to any disclaimer, the term of this patent is extended or adjusted under 35 U.S.C. 154(b) by 975 days.

(21) Appl. No.: 16/389,291

(22) Filed: Apr. 19, 2019

(65) Prior Publication Data

US 2020/0330766 A1  Oct. 22, 2020

(51) Int. Cl.
| | |
|---|---|
| *A61N 1/36* | (2006.01) |
| *A61B 17/34* | (2006.01) |
| *A61N 1/05* | (2006.01) |
| *A61N 1/372* | (2006.01) |
| *A61B 6/00* | (2006.01) |
| *A61B 90/00* | (2016.01) |
| *A61B 6/12* | (2006.01) |

(52) U.S. Cl.
CPC ............ *A61B 17/3401* (2013.01); *A61B 6/12* (2013.01); *A61B 6/487* (2013.01); *A61B 17/3468* (2013.01); *A61B 90/39* (2016.02); *A61N 1/0551* (2013.01); *A61N 1/36071* (2013.01); *A61N 1/37205* (2013.01); *A61B 2090/3966* (2016.02)

(58) Field of Classification Search
CPC ............ A61B 17/3401; A61B 17/3468; A61B 2090/3966; A61B 6/12; A61B 6/487; A61B 90/39; A61N 1/0551; A61N 1/0558; A61N 1/36071; A61N 1/37205; H01L 2224/81101; H01L 2924/07811; H05K 3/321

See application file for complete search history.

(56) References Cited

U.S. PATENT DOCUMENTS

| | | |
|---|---|---|
| 7,212,110 B1 | 5/2007 | Martin et al. |
| 7,571,007 B2 | 8/2009 | Erickson et al. |
| 8,934,981 B2 | 1/2015 | De Ridder |
| 8,983,624 B2 | 3/2015 | Imran |
| 9,498,634 B2 | 11/2016 | De Ridder |

(Continued)

*Primary Examiner* — George Manuel
(74) *Attorney, Agent, or Firm* — Norton Rose Fulbright US LLP

(57) ABSTRACT

In one embodiment, a method of implanting a stimulation lead to stimulate a dorsal root ganglion (DRG) of a patient, comprises: placing a distal portion of the stimulation lead within an implant tool; accessing the epidural space of the patient with the distal end of the implant tool; contacting a surface of a pedicle of the patient with a distal tip of the Implant tool above a foramen leading to a target DRG; after contacting the surface of the pedicle with the distal tip, advancing the stimulation lead from a side port of the implant tool, wherein the side port is located proximal to the distal tip of the implant tool; advancing the stimulation lead through the foramen to position one or more electrodes of the stimulation lead adjacent to the target DRG; and providing electrical stimulation to the target DRG to stimulate the target DRG using one or more electrodes of the stimulation lead.

20 Claims, 21 Drawing Sheets

(56) References Cited

U.S. PATENT DOCUMENTS

| | | | |
|---|---|---|---|
| 2006/0170486 A1 | 8/2006 | Tranchina et al. | |
| 2010/0179562 A1* | 7/2010 | Linker | A61N 1/0551 607/117 |
| 2010/0292769 A1* | 11/2010 | Brounstein | A61N 1/0551 607/117 |
| 2011/0276056 A1 | 11/2011 | Grigsby et al. | |

* cited by examiner

1400

METHODS OF IMPLANTING A STIMULATION LEAD FOR STIMULATION OF A DORSAL ROOT GANGLION

BACKGROUND

In 1959, neurosurgeon Willem Noordenbos reported that a signal carried along large diameter fibers may inhibit the signal carried by the thinner pain fibers. From this, Melzack and Wall proposed the "Gate-control" theory of pain. The Gate-control theory postulates that stimulation of large myelinated fibers suppresses the response of dorsal horn neurons to input from small, unmyelinated peripheral pain fibers. The Gate-control theory provided the theoretical foundation for the use of spinal cord stimulation (SCS) as a clinical treatment for chronic pain. The first experimental clinical use of SCS was shortly followed by clinical trials of SCS in patients suffering from intractable chronic pain in the early seventies.

In conventional SCS, an electrode is positioned over the spinal cord and connected to an internal pulse generator. All pulse generators currently available deliver tonic pulses that can be modified by altering the pulse width, frequency, and amplitude to get maximal pain suppression. The Internal pulse generators can use either constant voltage or constant current to modulate the underlying cells or networks. Electrical stimulation of large afferents of the dorsal column by an electrode placed dorsomedially in the epidural space elicits a tingling sensation (paresthesia) in the corresponding dermatomes. To obtain successful treatment of chronic neuropathic pain by conventional SCS, the stimulation-induced paresthesia must cover the pain area completely.

As illustrated in FIG. 1, prior art spinal column or spinal cord stimulators (SCS) commonly deliver electrical energy to the spinal cord through an elongate paddle 5 or epidural electrode array containing electrodes 6 positioned external to the spinal cord dura layer 32. The spinal cord dura layer 32 surrounds the spinal cord 13 and is filled with cerebral spinal fluid (CSF). The spinal cord 13 is a continuous body and three spinal levels 14 of the spinal cord 13 are illustrated. For purposes of illustration, spinal levels 14 are sub-sections of the spinal cord 13 depicting that portion where the dorsal and ventral roots join the spinal cord 13. The peripheral nerve 44 divides into the dorsal root 42 and dorsal root ganglion 40 and the ventral nerve root 41 each of which feed into the spinal cord 13. An ascending pathway 92 is illustrated between level 2 and level 1 and a descending pathway 94 is illustrated from level 2 to level 3. Spinal levels 14 can correspond to the vertebral levels of the spine commonly used to describe the vertebral bodies of the spine. For simplicity, each level illustrates the nerves of only one side and a normal anatomical configuration would have similar nerves illustrated in the side of the spinal cord 13 directly adjacent the paddle 5.

Typically, SCS are placed in the spinal epidural space. Conventional SCS systems are described in numerous patents. For example, the paddle 5 is about 8 mm wide and from 24 to 60 mm long depending upon how many spinal levels are stimulated. The illustrated electrode paddle 5 is adapted to conventionally stimulate all three spinal levels 14. These exemplary levels 1, 2 and 3 could be anywhere along the spinal cord 13. Positioning a stimulation paddle 5 in this manner results in the electrodes 6 spanning a plurality of nerves, here the dorsal root ganglion 40, the ventral root 41 and peripheral nerve 41 on multiple spinal levels More recent SCS therapies have been applied to address chronic pain in patients. One example is BurstDR™ stimulation (available in SCS systems of Abbott, Plano Tex.). This type of SCS has been reported to address chronic pain in patients without necessarily inducing paresthesia in patients. De Ridder D, Vanneste S, Plazier M, van der Loo E, Menovsky T., Burst Spinal Cord Stimulation: Toward Paresthesia-Free Pain Suppression, Neurosurgery 2010; 66:986-90.

The dorsal root ganglion (DRG) is a neural structure located at each segmental level of the spinal column in the lateral epidural space within the spinal foramen. The DRG contains the cell bodies of the primary sensory neurons. The DRG is involved in the transduction of pain to the central nervous system. It has been experimentally shown that electrical stimulation of the DRG reduces the excitability of the DRG neurons. It has been reported that incoming afferent pain signals spread over the different levels of the spinal cord and dorsal root ganglia and as a consequence communication between the segmental levels takes effect. The possible advantages of DRG stimulation include an improved ability to achieve pain relief in locations that are typically challenging to effectively achieve with SCS and enhanced stability of the stimulation regardless of body position.

3A illustrates a stimulation system with an electrode embodiment of the present Invention implanted into a dorsal root ganglion (DRG) of a spinal level.

Figure 3A:
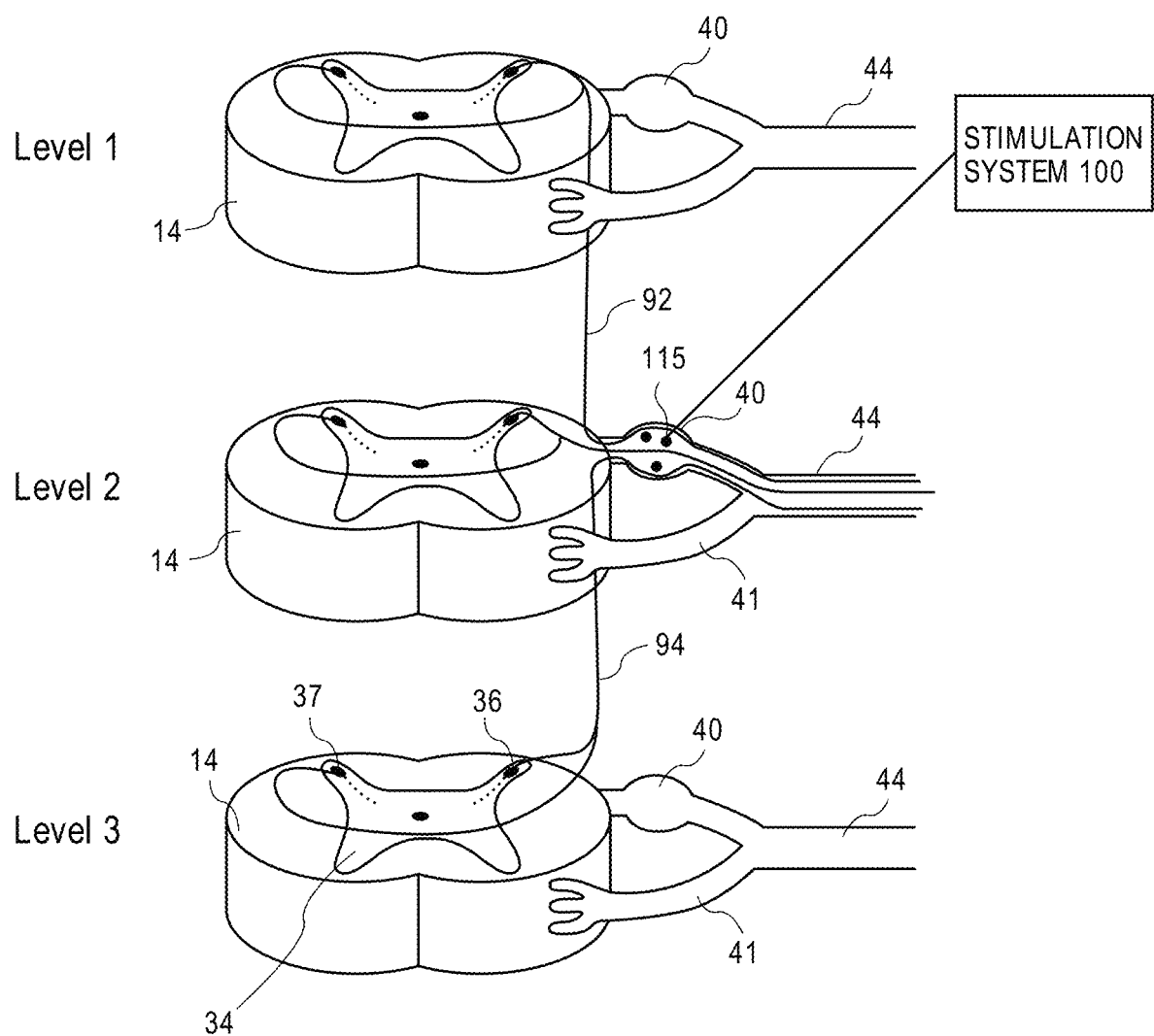
Figure 3B:
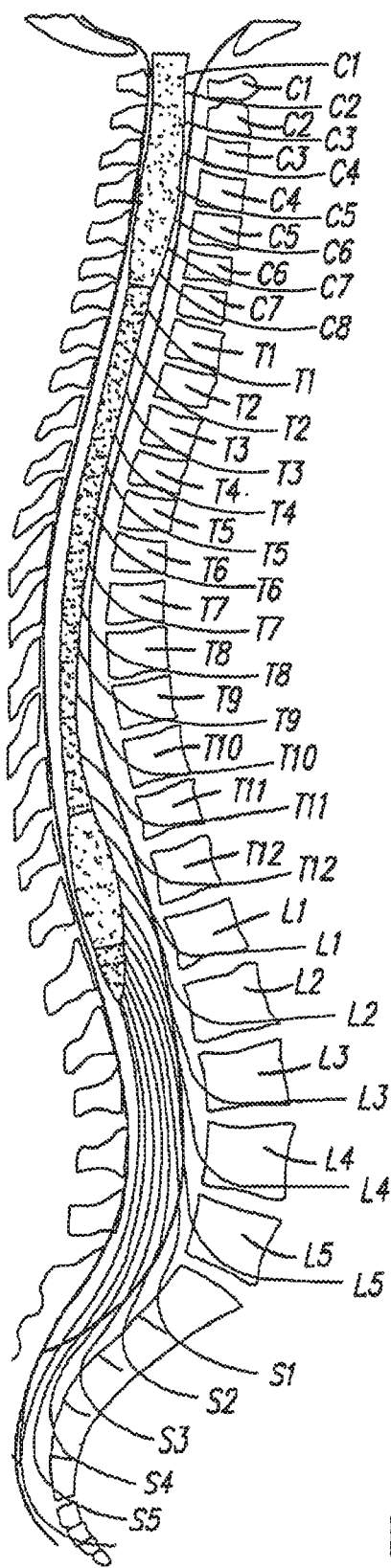

FIG. 3B relates the spinal nerve roots to their respective vertebral spinal levels.

Figure 3C:
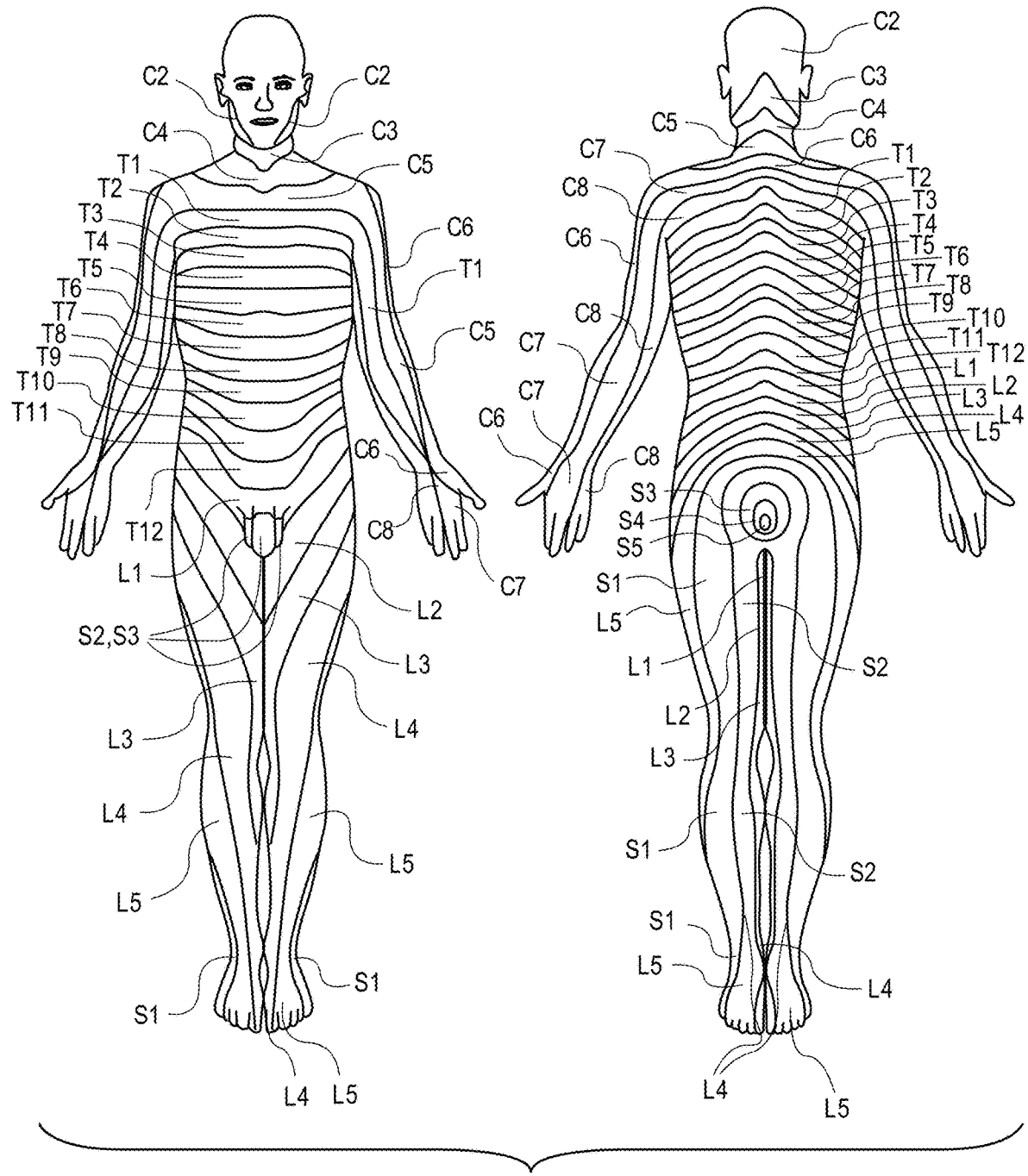

FIG. 3C illustrates the various dermatomes of the body related to their respective nerve roots in FIG. 3B.

Figure 4A:
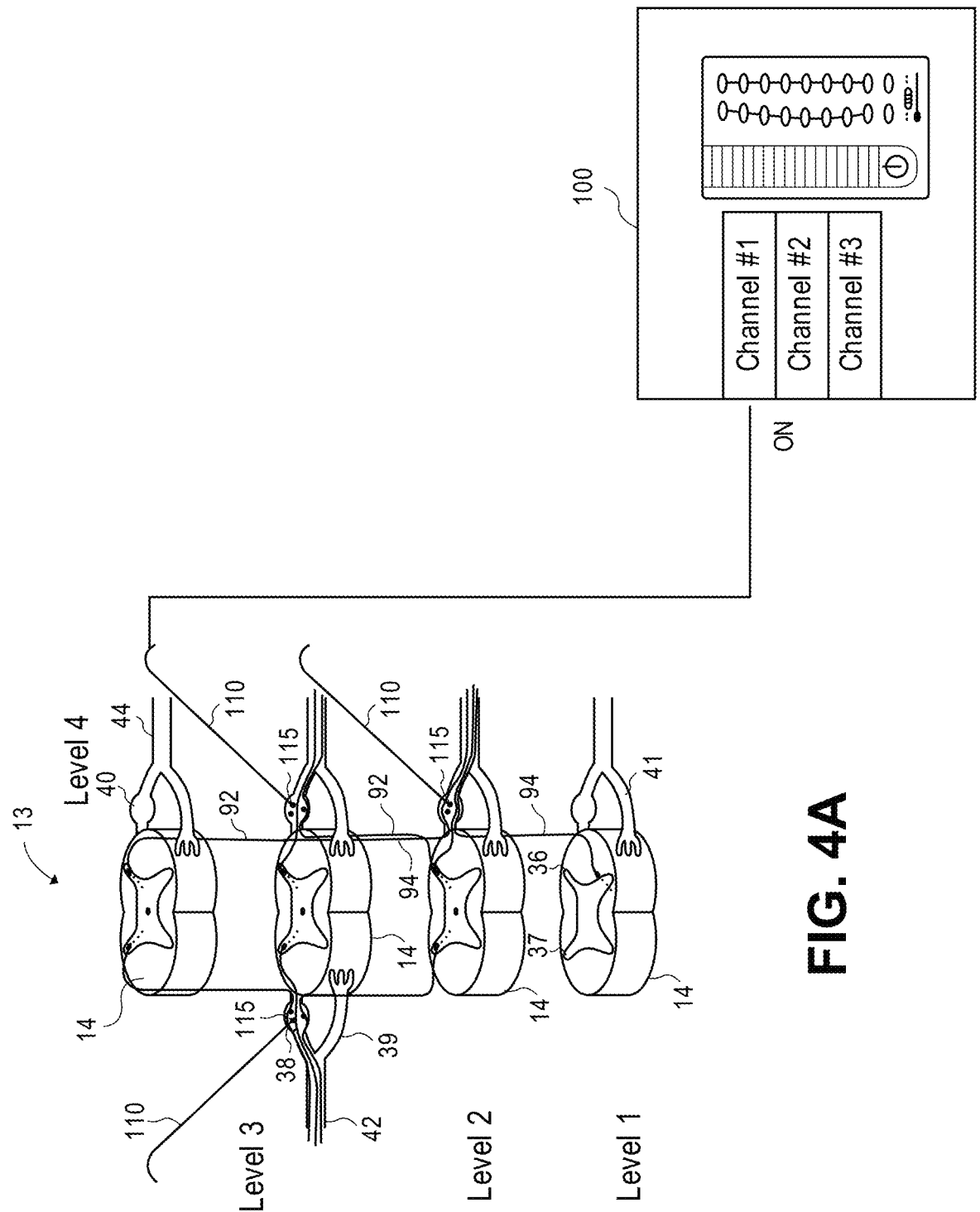
Figure 4B:
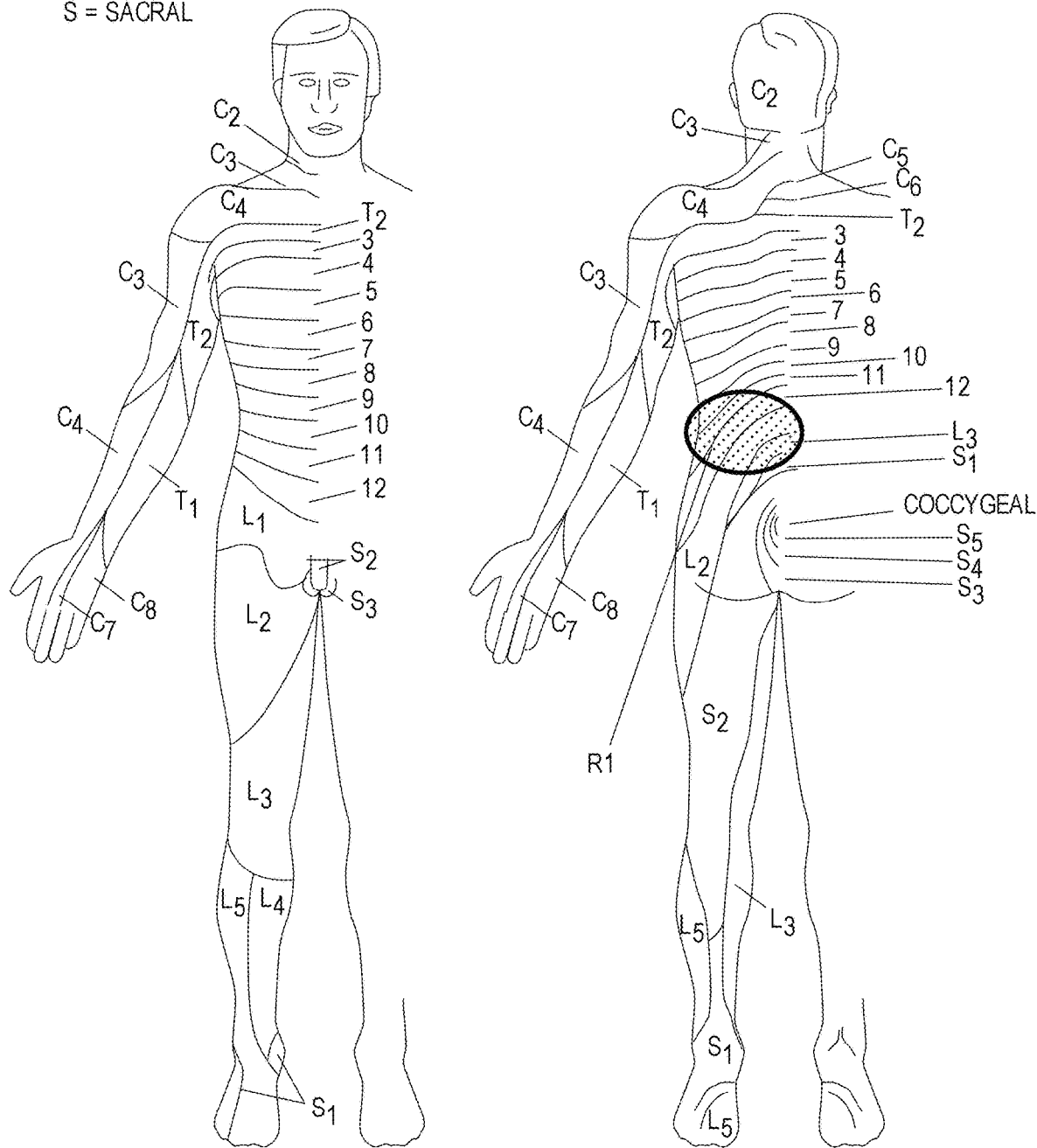

FIG. 4A illustrates a single electrode, single level activation pattern and FIG. 4B illustrates an exemplary corresponding dermatome to the stimulation pattern of FIG. 4A.

Figure 5A:
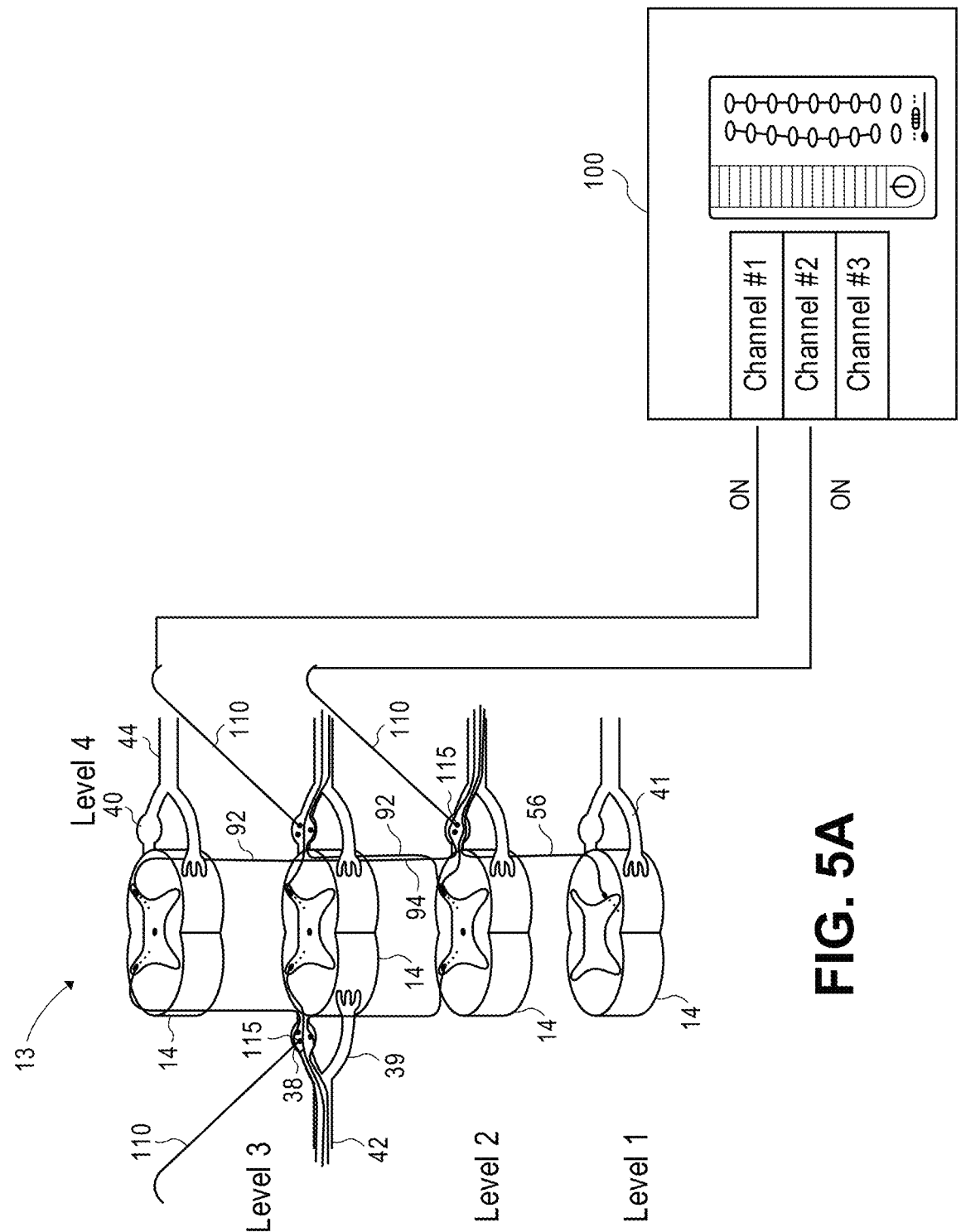
Figure 5B:
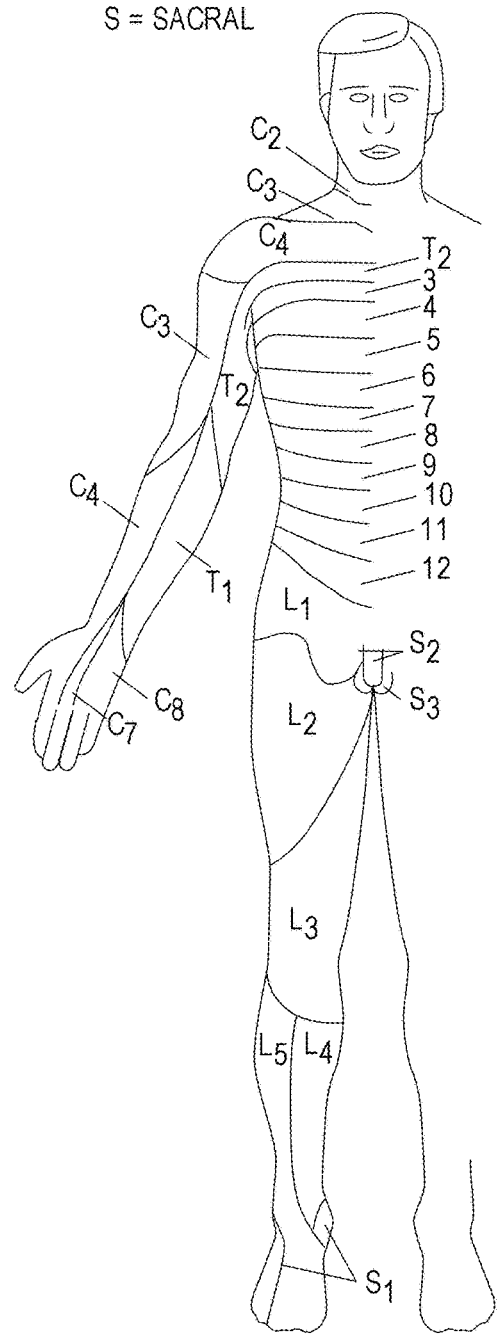
Figure 5B:
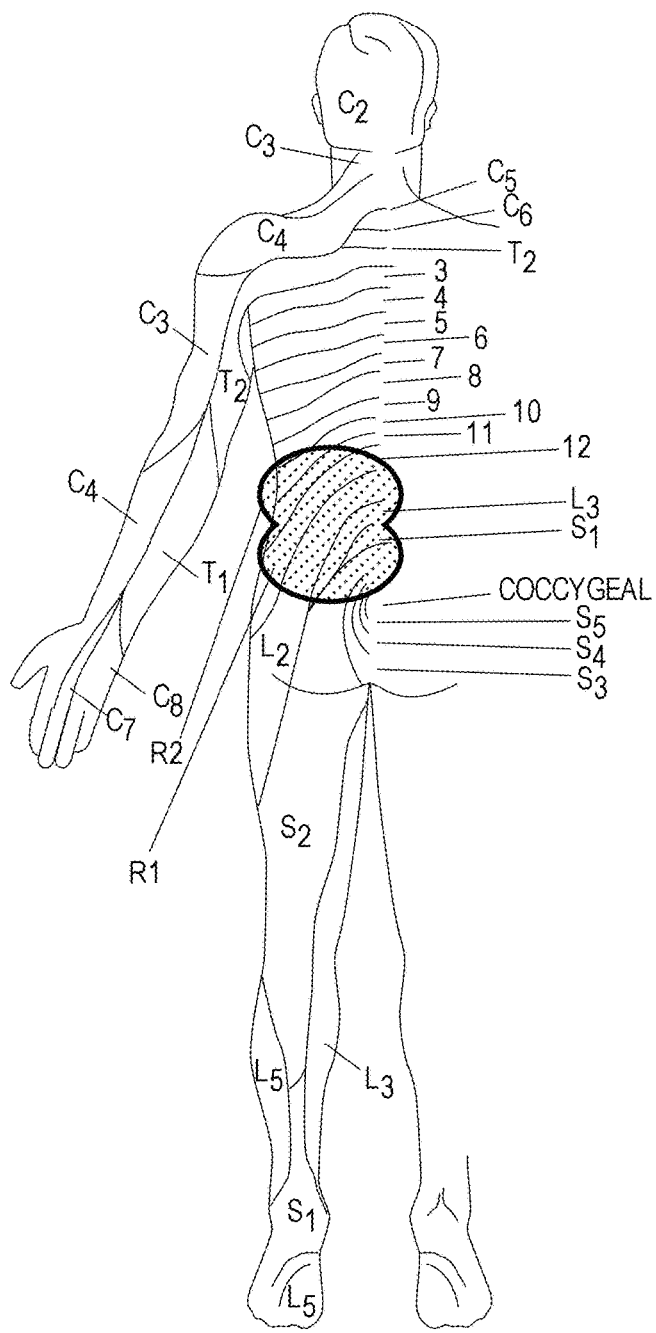

FIG. 5A illustrates a single electrode per level, two level activation pattern and FIG. 5B illustrates an exemplary corresponding dermatome to the stimulation pattern of FIG. 5A.

Figure 6A:
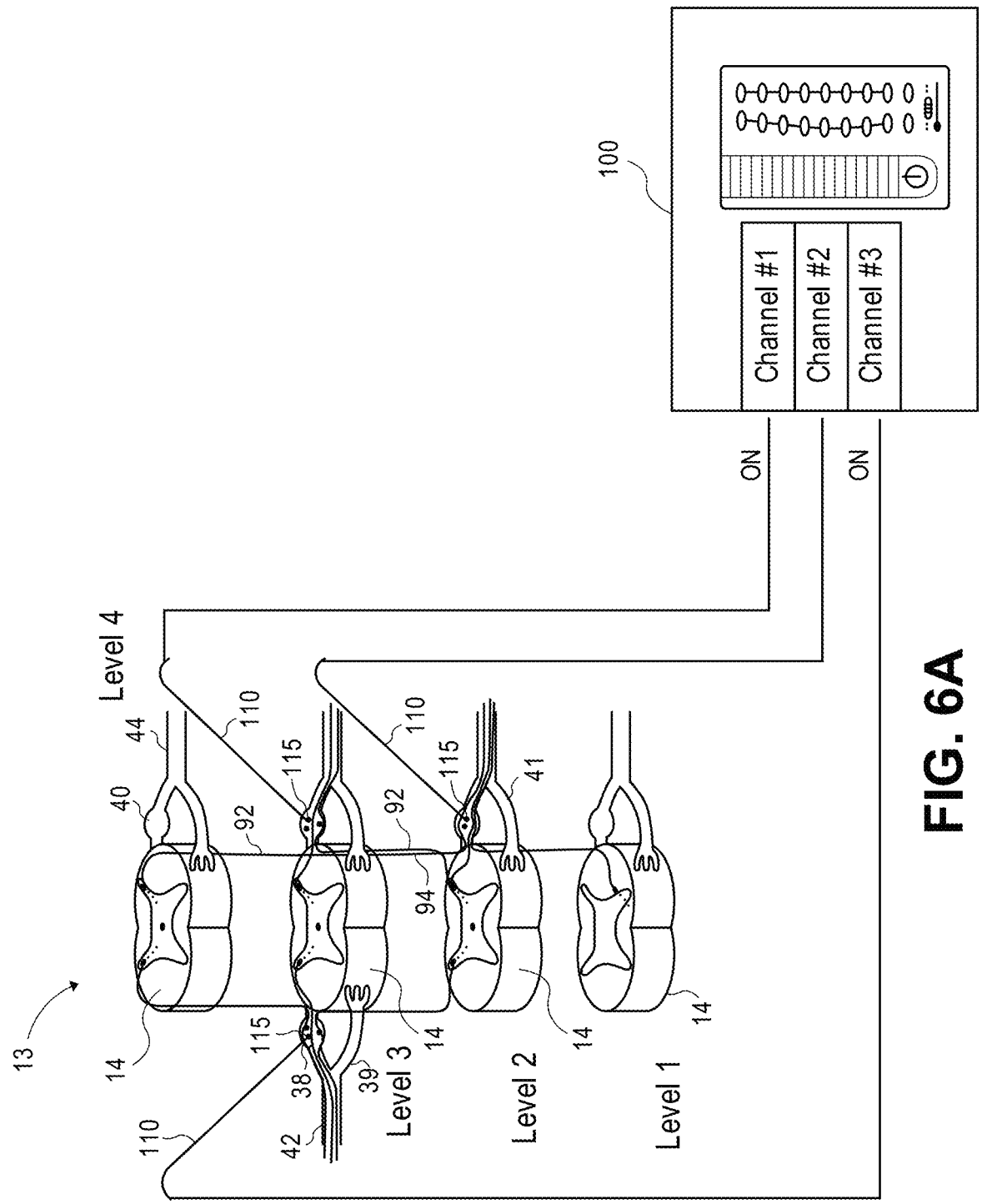
Figure 6B:
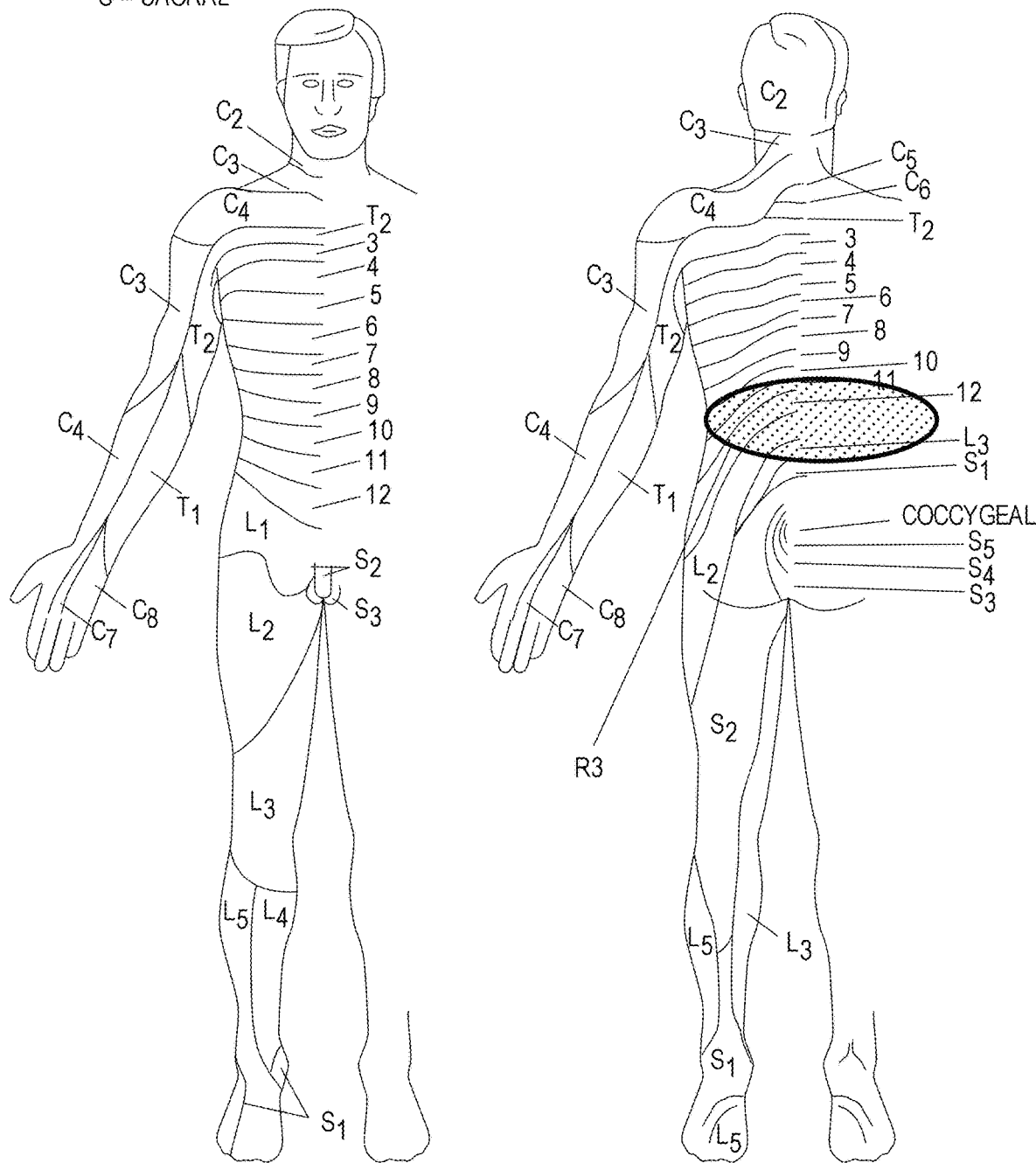

FIG. 6A Illustrates a two electrode, single level activation pattern and FIG. 6B illustrates an exemplary corresponding dermatome to the stimulation pattern of FIG. 6A.

Figure 7A:
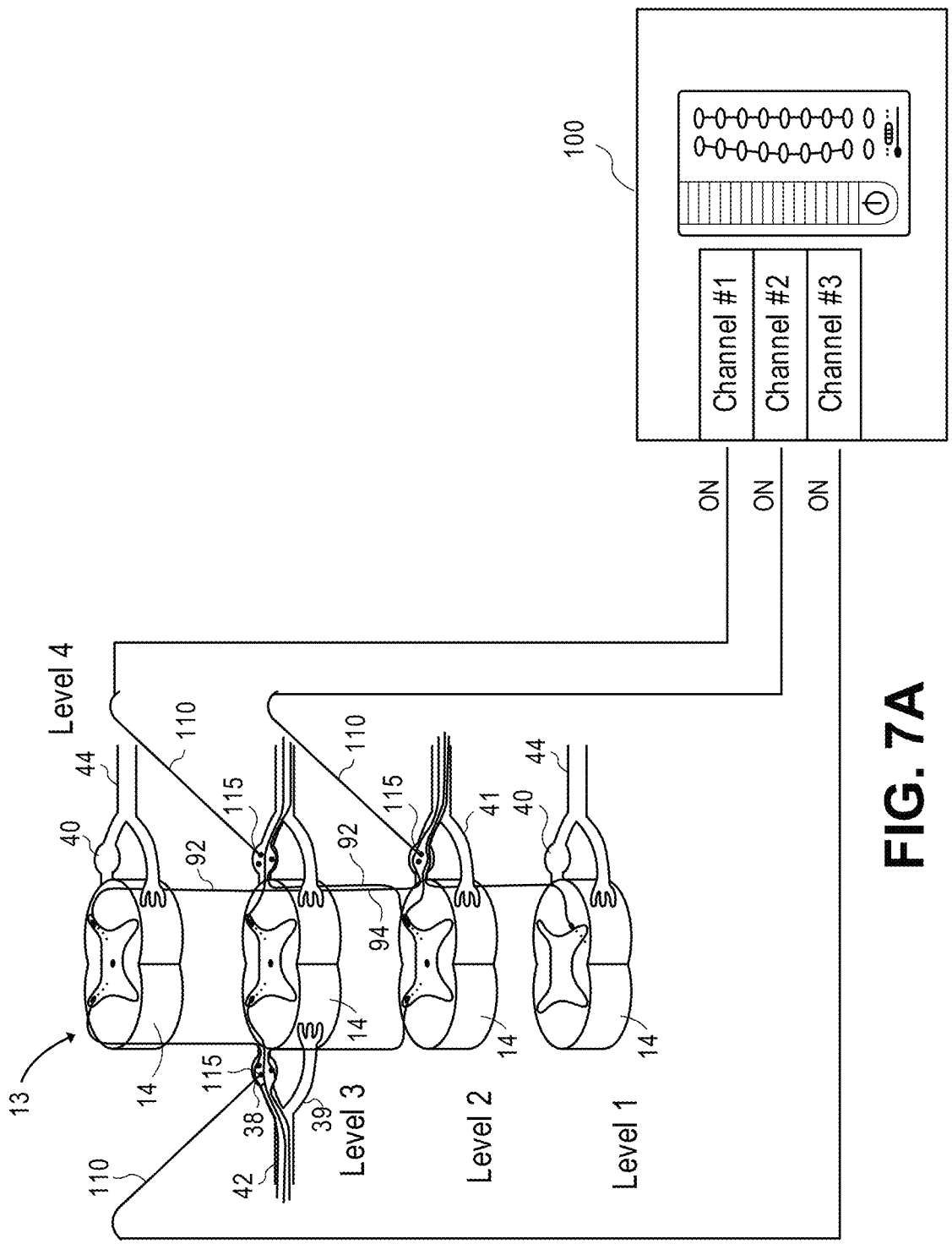
Figure 7B:
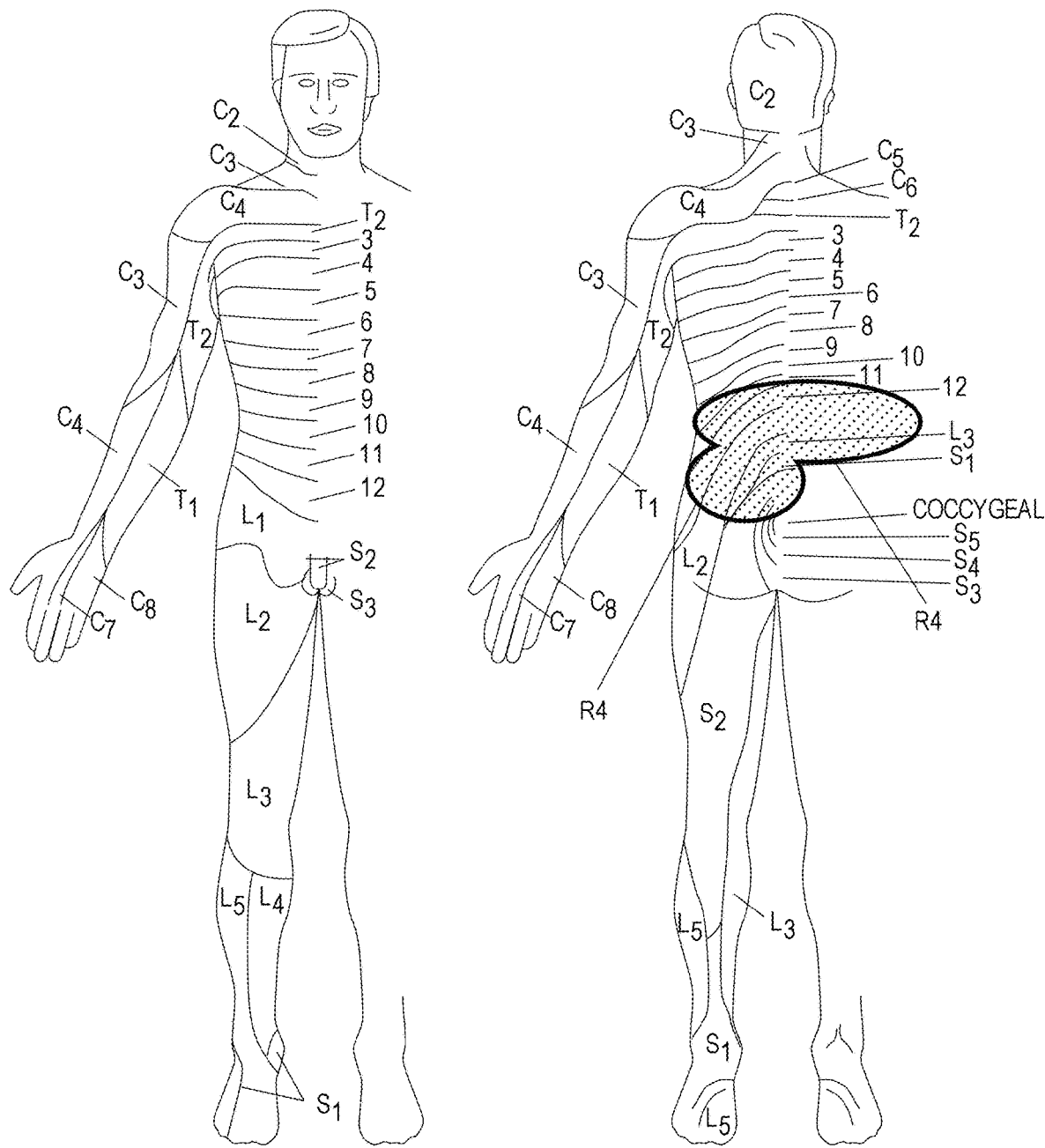

FIG. 7A illustrates a single electrode level and a two electrode level activation pattern and FIG. 7B illustrates an exemplary corresponding dermatome to the stimulation pattern of FIG. 7A.

Figure 8:
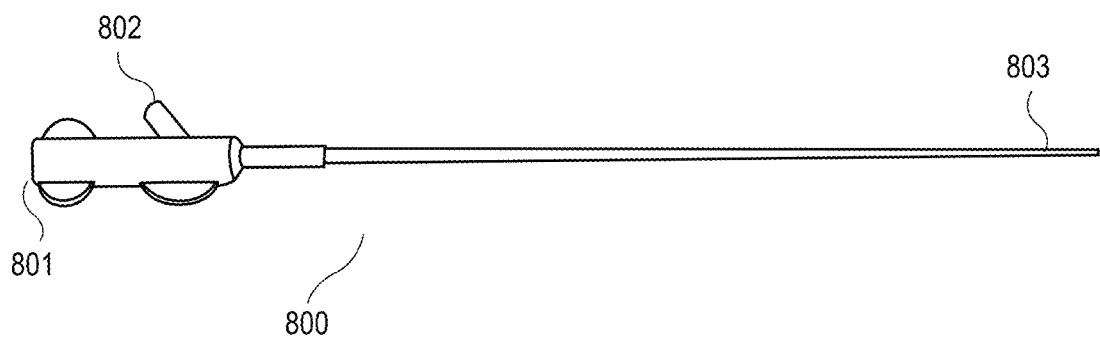

FIG. 8 depicts an implant tool for implanting a lead for DRG stimulation according to some embodiments.

Figure 9:
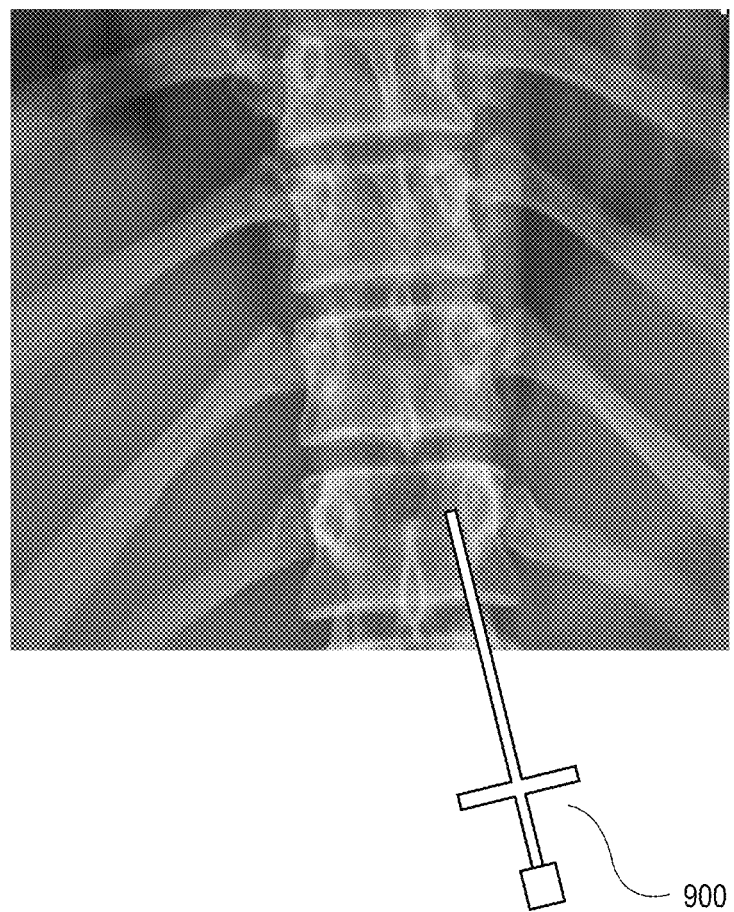

FIG. 9 depicts a needle positioned during an implant procedure according to some embodiments.

Figure 10:
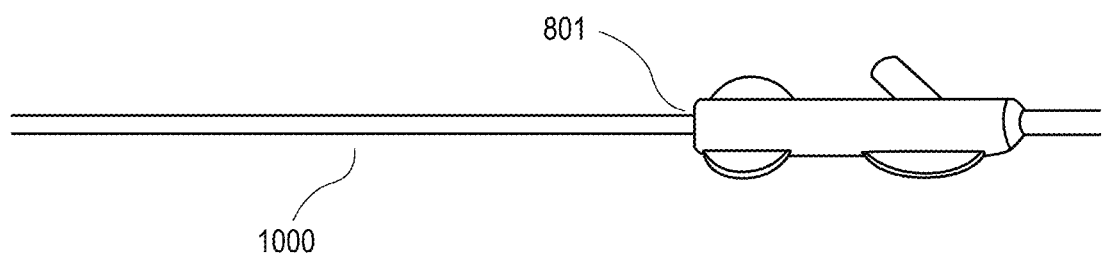

FIG. 10 depicts a DRG lead being placed in an implant tool according to some embodiments.

Figure 11:
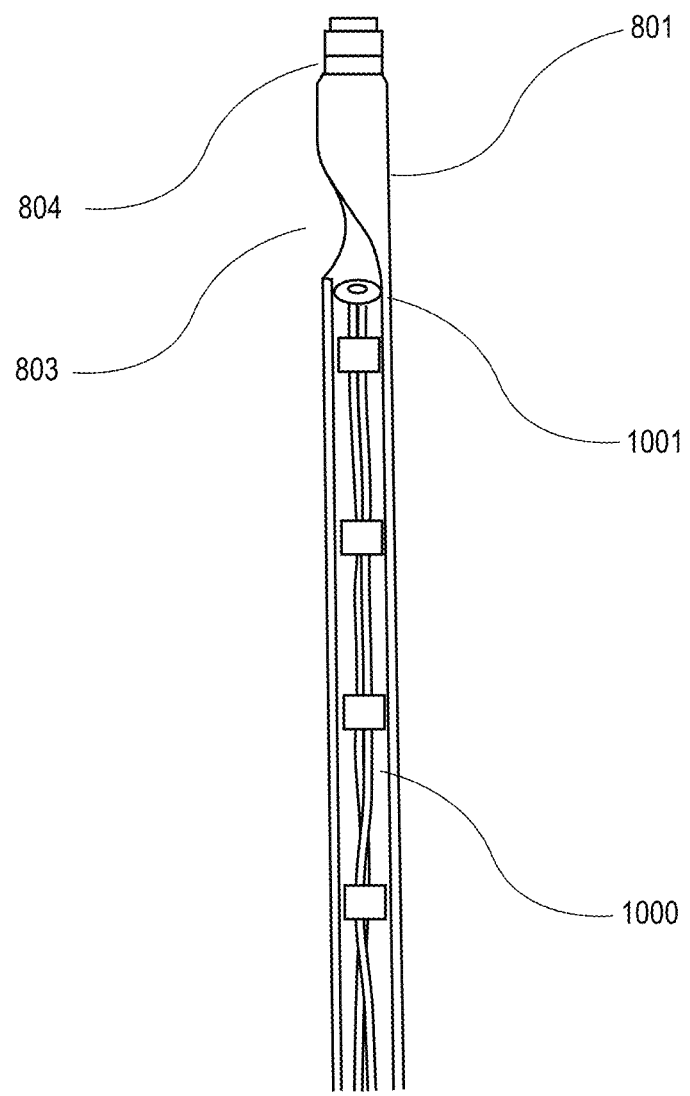

FIG. 11 depicts a distal end of the implant tool shown in FIG. 8 with a lead positioned therein for implant according to some embodiments.

Figure 12:
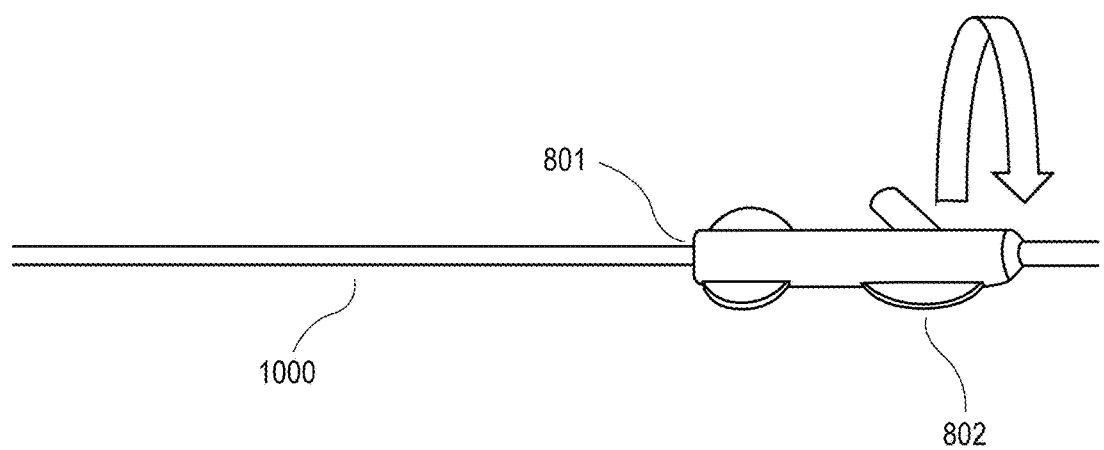

FIG. 12 depicts manipulation of the hub of the implant tool shown in FIG. 8 to lock the DRG in place according to some embodiments.

Figure 13:
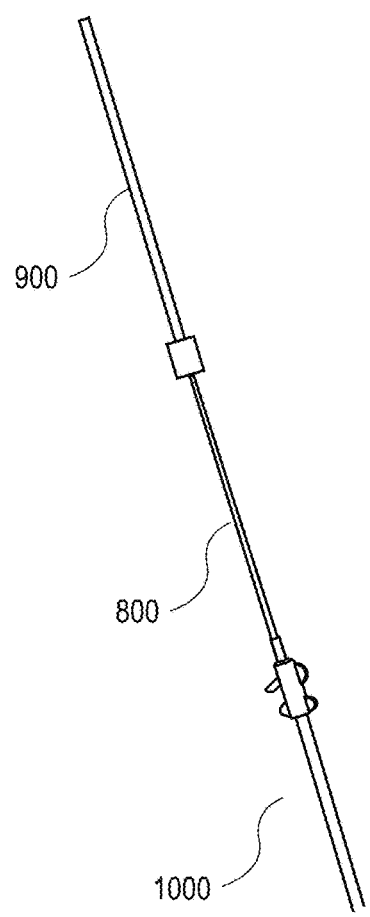

FIG. 13 depicts entry of the implant tool shown in FIG. 8 through a needle to access the epidural space according to some embodiments.

Figure 14:
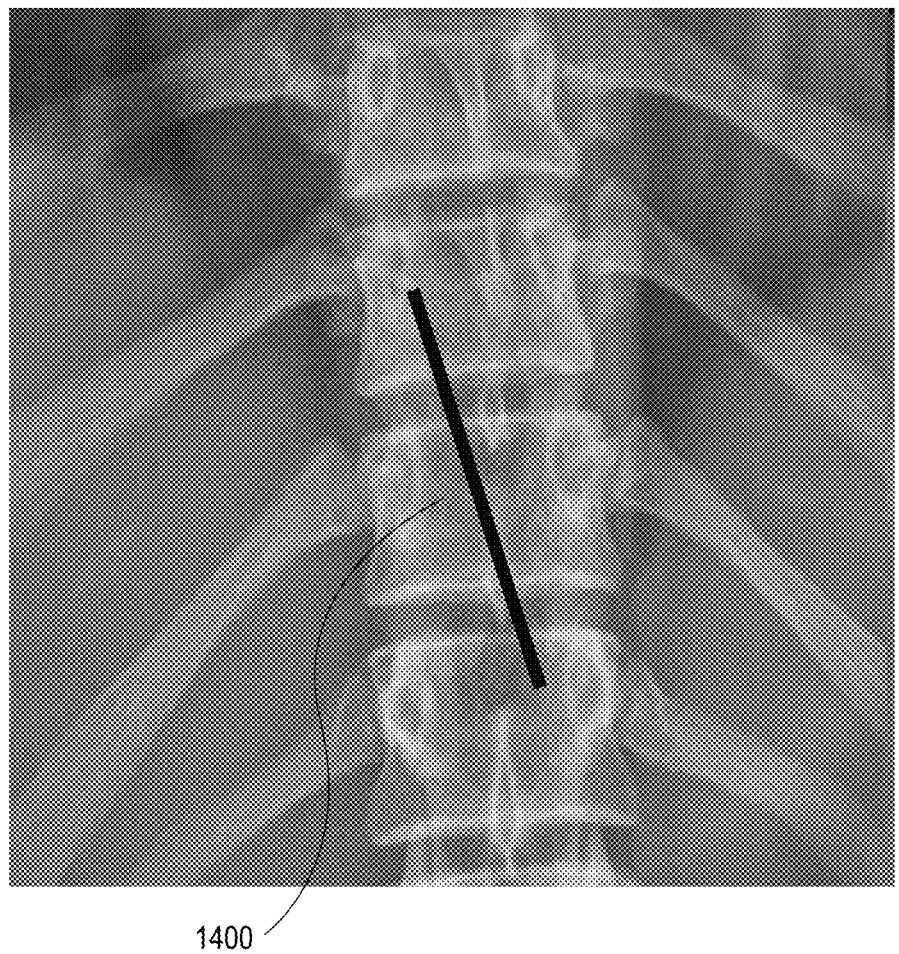

FIG. 14 depicts a path for advancement of the implant tool within the epidural space according to some embodiments.

Figure 15:
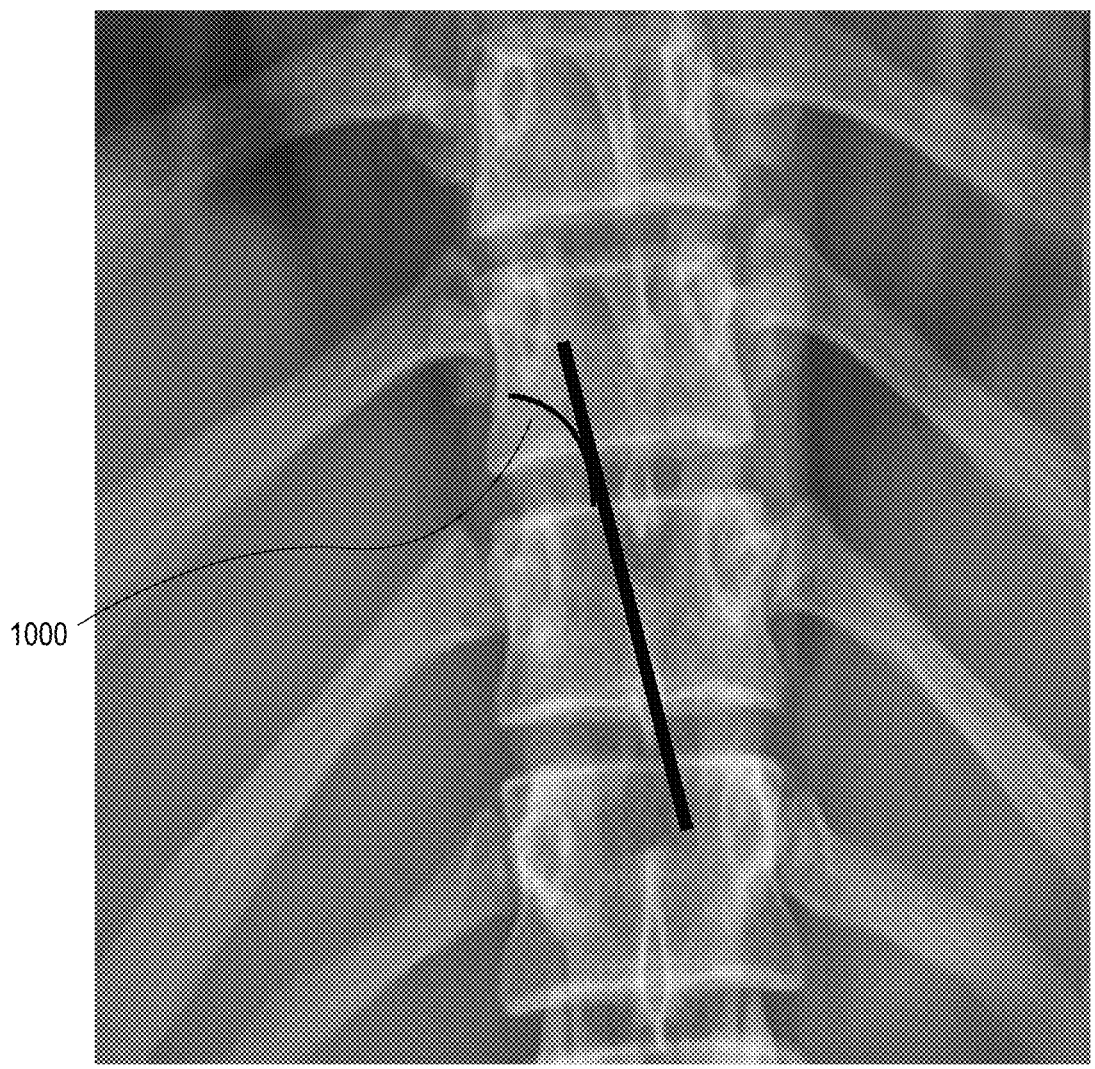

FIG. 15 depicts advancement of a DRG lead from the implant tool through a foramen according to some embodiments.

Figure 16:
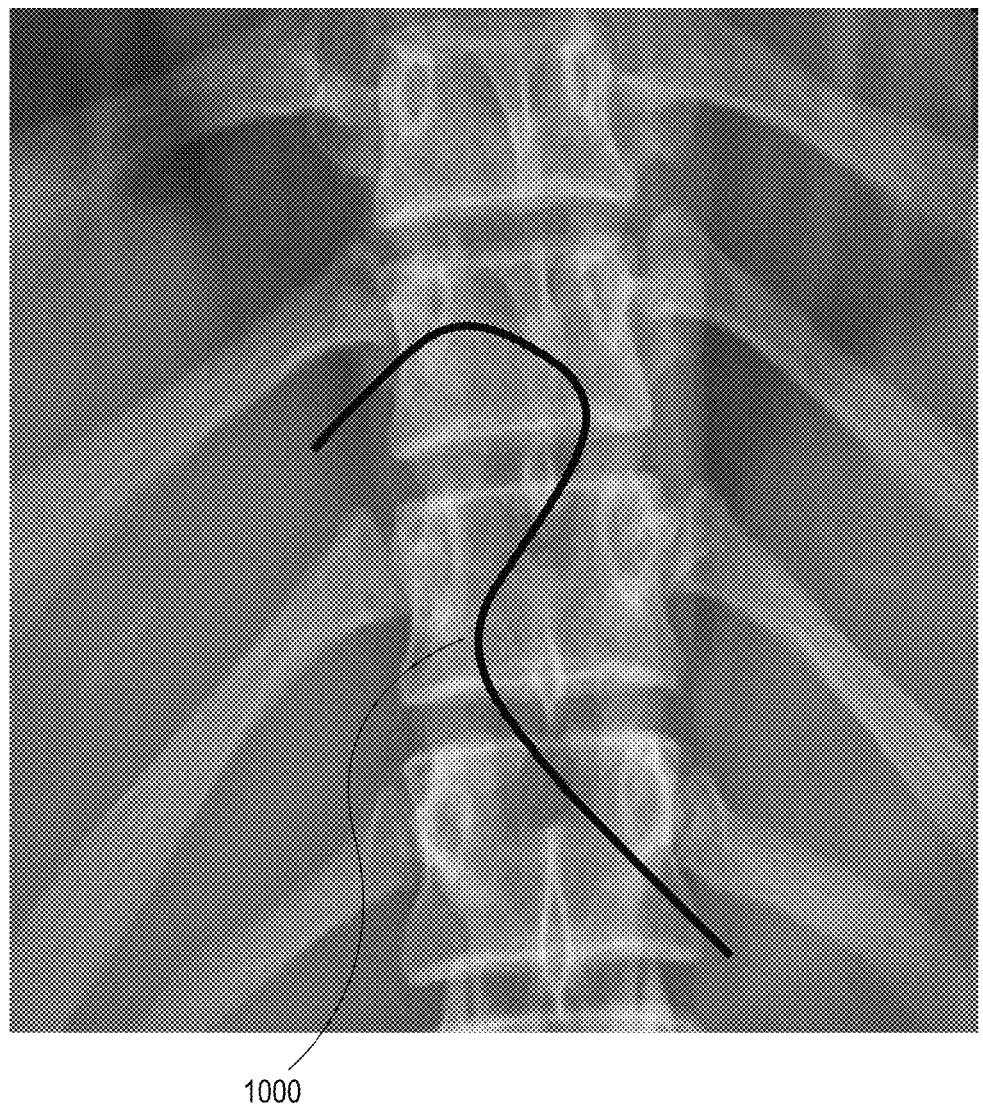

FIG. 16 depicts creation of an "S-loop" shape for the lead body of an implanted DRG lead to stabilize the DRG lead according to some embodiments.

Figure 17:
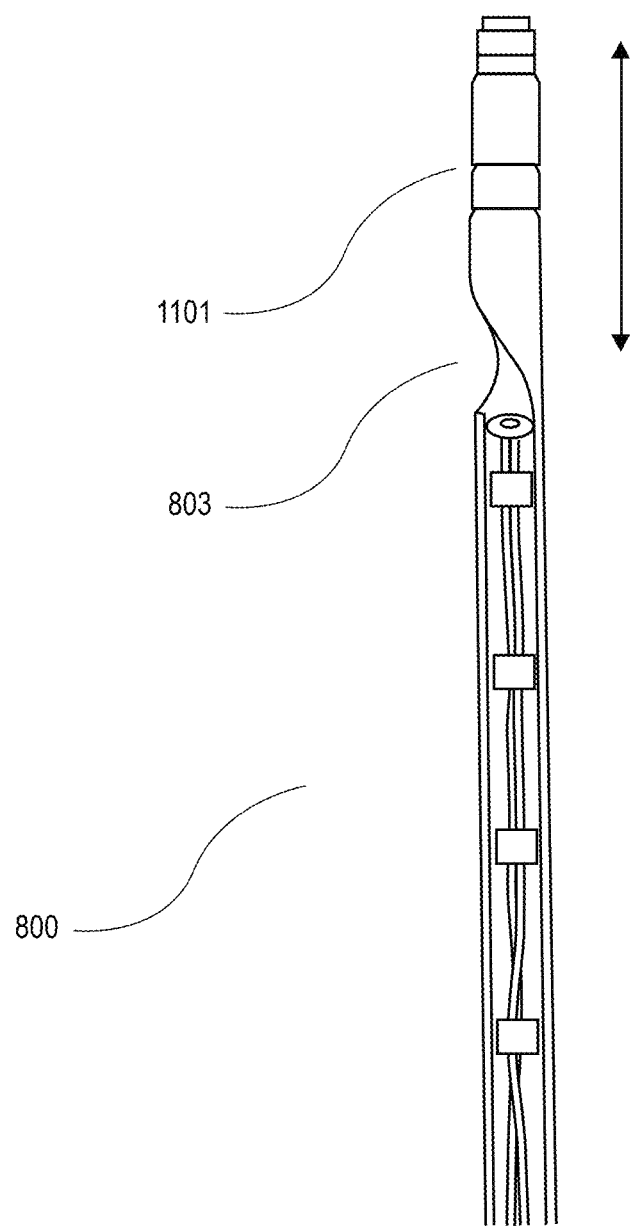

FIG. 17 depicts an implant tool with an adjustable distal tip according to some embodiments.

Figure 18:
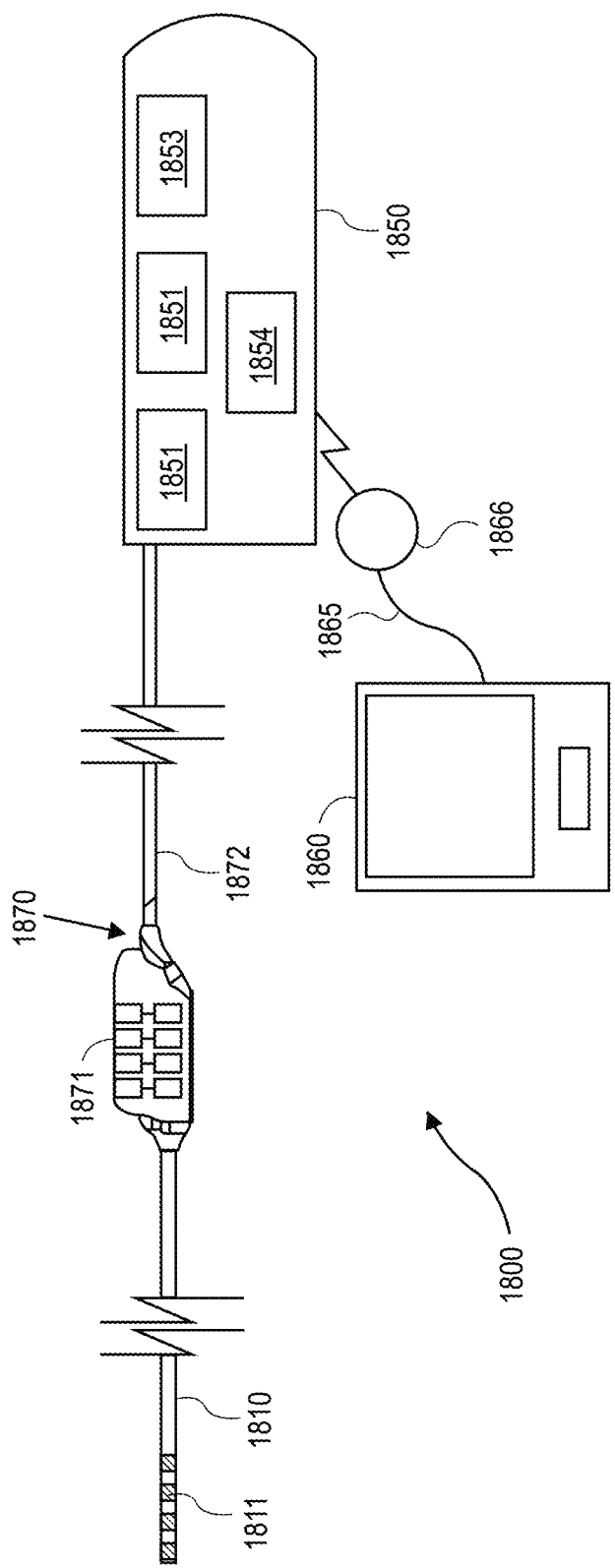

FIG. 18 depicts a system for stimulation one or more DRGs according to some embodiments.

DETAILED DESCRIPTION

Figure 1:
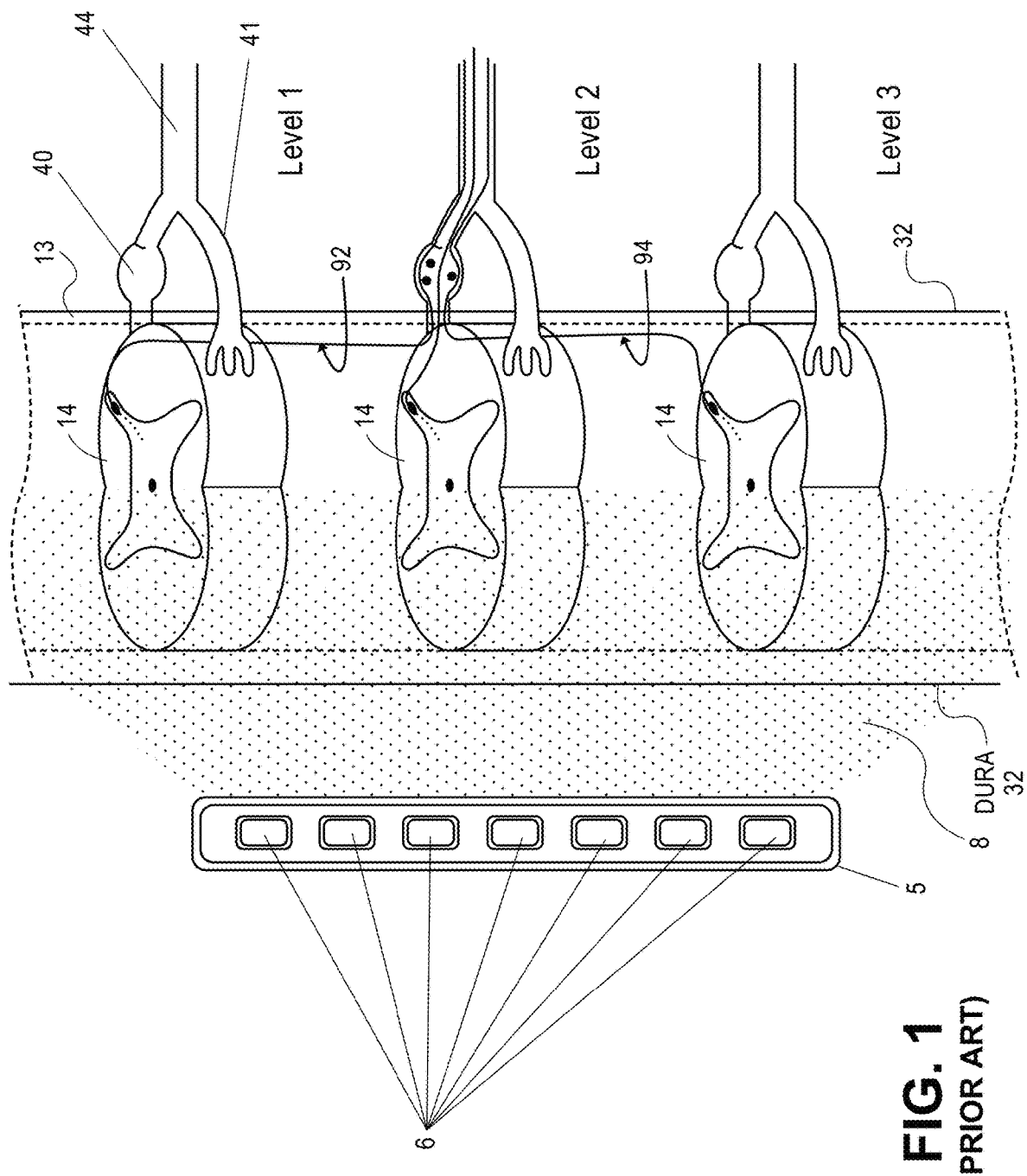
FIG. 1 illustrates a conventional epidural electrode array positioned external to and stimulating a portion of the spinal cord.
Figure 2A:
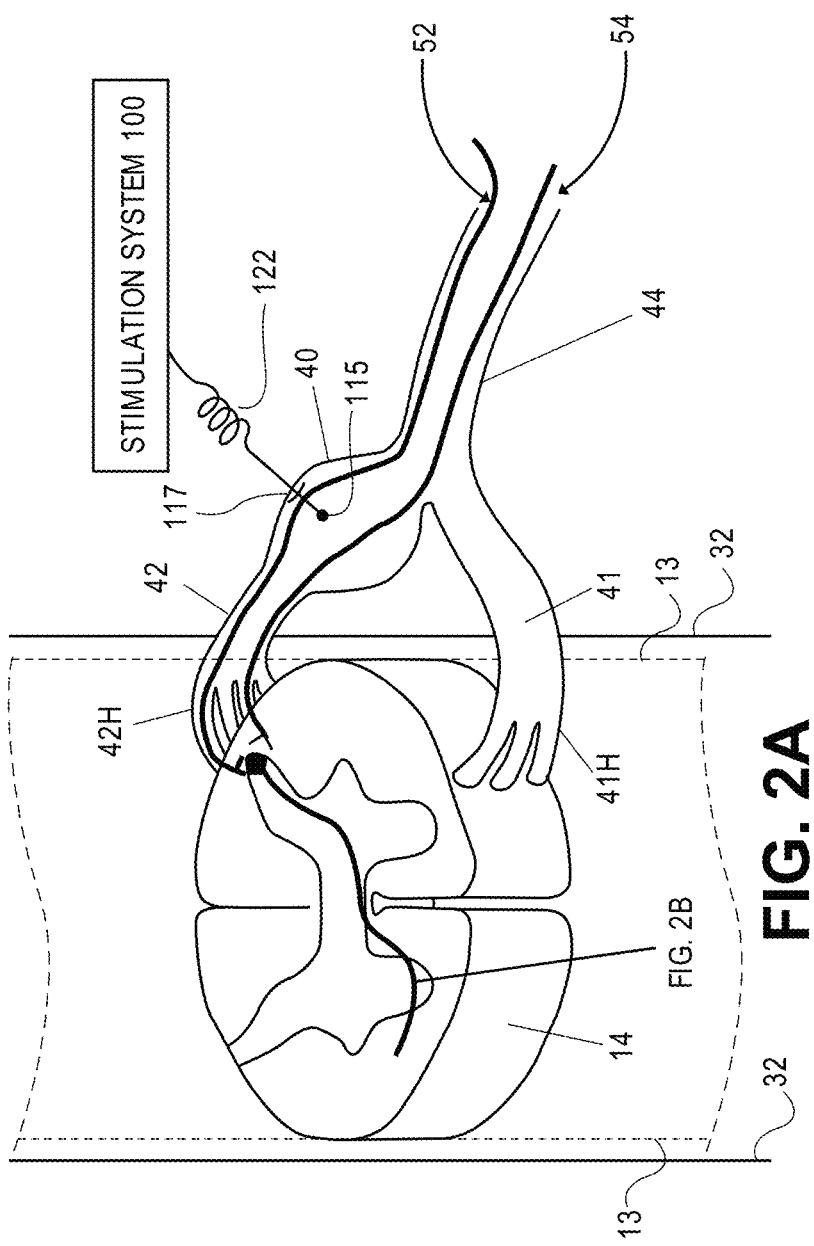
FIG. 2A illustrates an embodiment an electrode implanted into a spinal dorsal root ganglion.
Figure 2B:
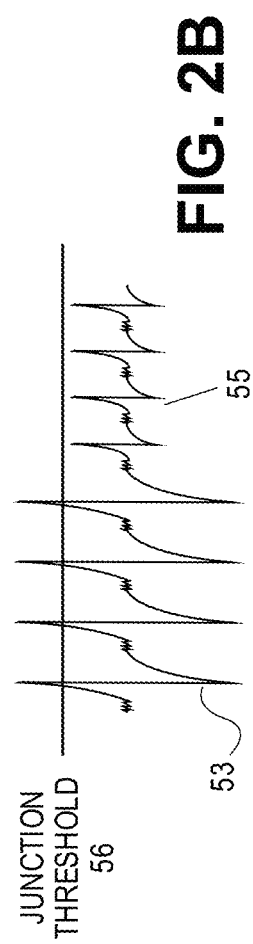
FIG. 2B Illustrates how selective stimulation techniques of FIG. 2A may raise a response threshold.

FIG. 2A illustrates an embodiment of a stimulation system 100 of the present invention in place with an electrode 115 implanted Into a spinal dorsal root ganglion 40. For purposes of illustration, spinal level 14, a sub-section of the spinal cord 13, is used to depict where the dorsal root 42 and ventral root 41 join the spinal cord 13, indicated by 42H and 41H respectively. The peripheral nerve 44 divides into the dorsal root 42 and dorsal root ganglion 40 and the ventral nerve root 41. For simplicity, the nerves of only one side are illustrated and a normal anatomical configuration would have similar nerves positioned on the other side. The spinal dura layer 32 surrounds the spinal cord 13 and is filled with cerebral spinal fluid (CSF). For clarity, the spinal dura layer or dura mater 32 alone is used to represent the three spinal meninges—the pia mater, the arachnoid mater and the dura mater—that surround and protect the spinal cord 13.

Note that the electrode 115 is implanted medial to the peripheral nerve 44 after the nerve root splits into the ventral nerve 41 containing the motor nerves and the dorsal root 42 containing the sensory nerves. The electrode 115 is also Implanted lateral of the dura layer 32. The advantageous placement of one or more electrode embodiments of the present invention enables selective stimulation of neural tissue, such as a nerve root ganglion, without stimulation of surrounding neural tissue. In this example, a dorsal root ganglion 40 is stimulated with little or imperceptible amounts of stimulation energy provided to the motor nerves within the ventral nerve root 44, portions of the spinal cord 13, spinal level 14, or the peripheral nerve 44. Embodiments of the present invention are particularly well suited for providing pain control since the sensory fibers running through the dorsal root ganglion 40 may be specifically targeted. Advantageously, embodiments of the present invention may neuromodulate one or more the dorsal root ganglia for pain control without influencing surrounding tissue.

The stimulation system 100 includes a pulse generator that provides stimulation energy in programmable patterns adapted for direct stimulation of neural tissue using small area, high impedance microelectrodes. The level of stimulation provided is selected to preferentially stimulate the A$\beta$ and A$\alpha$ fibers 52 over the c-fibers 54. Stimulation energy levels used by embodiments of the present invention utilize lower stimulation energy levels than conventional non-direct, non-specific stimulations systems because the electrode 115 is advantageously placed on, in or about a dorsal root ganglion 40. Based on conventional gate control theory, it Is believed that by stimulating of the faster transmitting A$\beta$ and A$\alpha$ fibers 52 by the stimulation methods of the present invention, the signal 53 from the fibers 52 will release opiates at the junction of the dorsal root 42 and the spinal cord 13. This release raises the response threshold at that junction (elevated junction threshold 56). The later arriving c-fiber signal 55 remains below the elevated junction threshold 56 and goes undetected.

Accordingly, some embodiments of the present invention provide selective stimulation of the spinal cord, peripheral nervous system and/or one or more dorsal root ganglia. As used herein in one embodiment, selective stimulation means that the stimulation substantially only neuromodulates or neurostimulates a nerve root ganglion. In one embodiment, selective stimulation of a dorsal root ganglion leaves the motor nerves unstimulated or unmodulated. In addition, in other embodiments, selective stimulation can also mean that within the nerve sheath, the A-myelinated fibers are preferentially stimulated or neuromodulated as compared to the c-unmyelinated fibers. As such, embodiments of the present invention advantageously utilize the fact that A-fibers carry neural impulses more rapidly (almost twice as fast) as c-fibers. Some embodiments of the present invention are adapted to provide stimulation levels intended to preferentially stimulate A-fibers over c-fibers.

In additional embodiments, selective stimulation can also mean that the electrode (including an electrode coated with or adapted to deliver a pharmacological agent) is in intimate contact with the tissue or other nervous system component that is the subject of stimulation. This aspect recognizes our advantageous use of electrode placement. In specific illustrative embodiments discussed further below; one or more stimulation electrodes are placed (1) against or in contact with the outer sheath of a nerve root ganglion; (2) within a nerve root ganglion; (3) within the root ganglion interfascicular space; (4) in contact with a portion of the spinal cord; (5) in a position that requires piercing of the epidural space, the dura, nerve root epinurium or a portion of the spinal cord; (6) in contact with a portion of the sympathetic nervous system or (7) in contact with neural tissue targeted for direct stimulation.

Moreover, selective stimulation or neuromodulation concepts described herein may be applied in a number of different configurations. Unilateral (on or in one root ganglion on a level), bilateral (on or in two root ganglion on the same level), unilevel (one or more root ganglion on the same level) or multi-level (at least one root ganglion is stimulated on each of two or more levels) or combinations of the above including stimulation of a portion of the sympathetic nervous system and one or more dorsal root ganglia associated with the neural activity or transmission of that portion of the sympathetic nervous system. As such, embodiments of the present invention may be used to create a wide variety of stimulation control schemes, individually or overlapping, to create and provide zones of treatment.

FIG. 3A illustrates an embodiment of a stimulation system 100 of the present Invention with an electrode 115 implanted into a dorsal root ganglion (DRG) 40. The figure illustrates three representative spinal levels 14 (i.e., spinal levels 1-3) of the spinal cord 13. The peripheral nerve 44 feeds into the dorsal root ganglion 40 and the ventral nerve root 41 each of which feed into the spinal cord 13. The dorsal horns 37, 36 are also indicated. For clarity, the dura 32 and complete spinal cord 13 are not Illustrated but are present as described elsewhere in this application and as occur in human anatomy. These exemplary levels 1, 2 and 3 could be anywhere along the spinal cord 13. For simplicity, each level illustrates the nerves of only one side.

Using level 2 as a reference, an ascending pathway 92 is illustrated between level 2 and level 1 and a descending pathway 94 is illustrated from level 2 to level 3. Application of stimulation energy or signals to the DRG 40 in level 2 may be used to block signals progressing upstream from level 2 towards the path/pathways 92. Moreover, modulation applied to portions of level 2 but may also be used to effectively block the neuron paths/pathways from another level (here, alternatively using levels 1 and/or 3) from reaching the brain. As such, application of stimulation to the level 2 DRG 40 using an embodiment of an apparatus and/or method of the present invention may advantageously provide an effective block of intrasegment pain pathways as well. It is to be appreciated that while three continuous levels are illustrated, some embodiments of the present invention may be used to stimulate 2 or more adjacent levels and still other embodiments may be used to stimulate 2 or more non-adjacent levels, or combinations thereof.

FIG. 3B relates the spinal nerve roots to their respective vertebral spinal levels. The letter C designates nerves and vertebrae in the cervical levels. The letter T designates vertebrae and nerves in the thoracic levels. The letter L designates vertebrae and nerves in the lumbar levels. The letter S designates vertebrae and nerves in the sacral levels. FIG. 3C illustrates the various dermatomes of the body related to their respective nerve roots using the designations in FIG. 3B.

FIGS. 4-7 illustrate one embodiment of a stimulation system activated under a variety of control conditions to provide different levels and degrees of pain control. FIGS. 4A, 5A, 6A and 7A all illustrate the stimulation system in various degrees of activation. FIGS. 4B, 5B, 6B and 7B illustrate a correspondingly Influenced dermatome.

FIGS. 4A, 5A, 6A and 7A illustrate a stimulation system 100 having 3 electrodes 115 implanted into dorsal root ganglia 40 on two adjacent spinal levels. For simplicity, each spinal level illustrates a dorsal root ganglion 40, a ventral root 41 and a peripheral nerve 44. The exception is spinal level 3 that illustrates an additional dorsal root ganglion 38, a ventral root 39 and a peripheral nerve 42. The three electrodes 115 are designated channels 1, 2 and 3 by the controller 106. Each electrode is activated to provide modulation energy or signals under the control of the controller 106. Exemplary electrodes for implantation into a nerve root ganglion are further described with regard to FIG. 18. Level 3 is an example of bilateral electrode placement and level 2 is an example of unilateral electrode placement. As such, the illustrated embodiment is a multi-level, unilateral and bi-lateral stimulation system. Stimulation energy is provided by a pulse generator (not illustrated but described in greater detail below in FIG. 18) under control of a suitable neurostimulation controller 106. Those of ordinary skill will recognize that any of a wide variety of known neurostimulation controllers may be used. Not illustrated in this view but present in the system are suitable connections between the various electrodes 115, electrode leads 110 and the controller 106. In the illustrations that follow, a line connecting the electrode lead 110 to the controller 106 indicates "stimulation on" communication from the controller 106 to one electrode 115 (see FIG. 4A) or more than one electrode 115 (see FIG. 5A).

A signal of "stimulation on" indicates any of a wide variety of stimulation patterns and degrees of stimulation. The "stimulation on" signal may be an oscillating electrical signal may be applied continuously or intermittently. Furthermore, if an electrode is implanted directly into or adjacent to more than one ganglion, the oscillating electrical signal may be applied to one electrode and not the other and vice versa. One can adjust the stimulating poles, the pulse width, the amplitude, as well as the frequency of stimulation and other controllable electrical and signally factors to achieve a desired modulation or stimulation outcome.

The application of the oscillating electrical signal stimulates the area of the nerve chain where the electrode 115 is placed. This stimulation may either increase or decrease nerve activity. The frequency of this oscillating electrical signal is then adjusted until the symptoms manifest by physiological disorder being treated has been demonstrably alleviated. This may step may be performed using patient feedback, sensors or other physiological parameter or indication. Once identified, this frequency is then considered the ideal frequency. Once the ideal frequency has been determined, the oscillating electrical signal is maintained at this ideal frequency by storing that frequency in the controller.

In one specific example, the oscillating electrical signal is operated at a voltage between about 0.5 V to about 20 V or more. More preferably, the oscillating electrical signal is operated at a voltage between about 1 V to about 30 V or even 40V. For micro stimulation, it is preferable to stimulate within the range of 1V to about 20V, the range being dependent on factors such as the surface area of the electrode. Preferably, the electric signal source is operated at a frequency range between about 10 Hz to about 1000 Hz. More preferably, the electric signal source is operated at a frequency range between about 30 Hz to about 500 Hz. Preferably, the pulse width of the oscillating electrical signal is between about 25 microseconds to about 500 microseconds. More preferably, the pulse width of the oscillating electrical signal is between about 50 microseconds to about 300 microseconds.

The application of the oscillating electrical signal may be provided in a number of different ways including, but not limited to: (1) a monopolar stimulation electrode and a large area non-stimulating electrode return electrode; (2) several monopolar stimulating electrodes and a single large area non-stimulating return electrode; (3) a pair of closely spaced bi-polar electrodes; and (4) several pairs of closely spaced bi-polar electrodes. Other configurations are possible. For example, the stimulation electrode(s) of the present invention may be used in conjunction with another non-stimulating electrode—the return electrode—or a portion of the stimulation system may be adapted and/or configured to provide the functionality of a return electrode. Portions of the stimulation system that may be adapted and/or configured to provide the functionality of the return electrode include, without limitation, the battery casing or the pulse generator casing.

In the illustrated configuration, a stimulation pattern provided to one of the electrodes positioned in level 3 (i.e., channel #1 "ON") produces pain blocking/relief in the indicated region of the body (i.e., shaded area R1) in FIG. 4B.

It will be appreciated that embodiments of the present invention can stimulate specific dermatome distributions to probe which electrode or group of electrodes or combination of electrodes (including drug coated or delivery electrodes) is best positioned or correlates most closely to one or more specific areas of pain. As such, a stimulation system according to an embodiment of the present invention may be "fine tuned" to a specific area of coverage or type of pain. The results obtained from such testing can be used to one or more stimulation or treatment regimes (i.e., series of stimulations in the presence of or in combination with a therapeutic agent from a coated electrode) for a particular patent for a particular type of pain. These pain treatment regimes may be programmed into a suitable electronic controller or computer controller system (described below) to store the treatment program, control and monitor the system components execution of the stimulation regime as the desired therapeutic regime is executed.

FIG. 5A provides another example of distribution of pain relief using a multi-channel stimulation system and method. In the illustrated configuration and stimulation pattern, a stimulation pattern is provided to one electrode each in levels 2 and 3 via channels #1 and #2. This stimulation electrode pattern provides pain blocking/relief in the indicated region of the body (i.e., areas R1, R2) of FIG. 5B.

FIG. 6A provides another example of distribution of pain relief using a multi-channel stimulation system and method. In the Illustrated configuration and stimulation pattern, a stimulation pattern provided to both electrodes in level 3 via channels #1 and #3 provides pain blocking/relief in the indicated region of the body (i.e., area R3) of FIG. 6B.

FIG. 7A provides another example of distribution of pain relief using a multi-channel stimulation system and method. In the illustrated configuration and stimulation pattern, a stimulation pattern Is provided to all electrodes in the system via channels #1, #2 and #3. This stimulation electrode pattern provides pain blocking/relief in the indicated region R4 of the body (i.e., FIG. 7B). It is to be appreciated that the electrode placement and blocking region patterns illustrated by FIGS. 4A-7B may be modified using information such as in FIGS. 3B and 3C for targeted placement to specific portions of the body depending upon individual needs.

Micro-electrode and stimulation system embodiments of the present invention may be implanted into a single nerve root ganglion utilizing the implantation methods of the present invention. The implantation methods described herein provide numerous advantages, including but not limited to: low risk percutaneous access route similar to other procedures, direct delivery of localized quantities of pharmacological agents at the nerve root when using embodiment having electrodes coated with pharmacological agents, and electrode placement that enables preferential, selective nerve fiber stimulation.

The implant of a stimulation lead in a position to stimulate the DRG can be a challenging procedure. During the typical implant process, a surgeon may manipulate an implant tool within the epidural space to place the distal tip of the implant tool immediately adjacent to the foramen associated with the DRG to be stimulation. The stimulation lead is then advanced and extended out from the distal tip of the implant tool to pass through the foramen into position adjacent to the DRG. However, the foramen is not directly visible under fluoroscopy. Instead, the surgeon estimates its position by identifying other vertebral structures that are visible via fluoroscopy.

In some embodiments, an implant tool is provided to assist the implant of a stimulation lead for DRG stimulation. FIG. 8 depicts implant tool 800 according to some embodiments. Implant tool 800 includes port 801 at its proximal end for receiving a stimulation lead to be implanted adjacent to a DRG. Implant tool 800 includes hub 802 for grasping the tool by the implanting clinician. Also, hub 802 may include a locking mechanism such that, when hub 802 is rotated, the locking mechanism of hub 802 locks onto the stimulation lead to prevent internal movement of the lead during positioning of the tool 800. Implant tool 800 includes side exit port 803 located slightly before the distal end of implant tool 800. Implant tool 800 may be fabricated from suitable medical grade polymers according to some embodiments.

In some embodiments, implant tool 800 is adapted for adjustment for the specific anatomy of a respective patient. In FIG. 17, implant tool 800 includes adjustable tip portion 1101. The length of adjustable tip portion 1101 may be shortened or lengthened by suitable manipulation of tool 800—e.g., using a twisting or sliding mechanism applied to the sheath of tool 800. As the length of adjustable tip portion 1101 is modified, the distance between exit port 803 and the end of the tool 800 changes. The clinician may change this distance depending upon the anatomy for a specific patient to ease the process of accessing the foramen when tool 800 is positioned relative to the medical aspect of the pedicle above the target foramen. The appropriate distance may be estimated, for example, by the clinician by observing the relative size of the respective vertebral segment using fluoroscopy and adjusting the distance by the variation of the actual size from an average value.

In some embodiments, the implant procedure begins by accessing the epidural space using a suitable needle 900 (e.g., a touhy needle) as shown in FIG. 9. The needle angle should be selected such that the eventual landing location of the distal tip of tool 800 will be the medial aspect of the pedicle above the target foramen for the DRG to be stimulated.

In some embodiments, stimulation lead 1000 is inserted through port 801 at the proximal end of tool 800 as shown in FIG. 10. The stimulation lead 1000 may include a removable stylet to assist manipulation of the distal portion of lead 1000 to position electrodes of the lead into a suitable position for DRG stimulation. Also, the stylet may include a curve or bias to assist the stimulation lead to curve or bend upon deployment from tool 800. Stimulation lead 1000 is then positioned within tool 800 such that tip 1001 of lead 1000 is near the end of the sheath of tool 800 but does not protrude from exit port 803 of tool 800 as shown in FIG. 11. Also, the end of tool 800 is shown in an enlarged view in FIG. 11 and includes radiopaque marker 804 at the distal end for visualization of the distal tip of tool under fluoroscopy. After the lead is correctly positioned within tool 800, hub 802 is rotated which engages the internal locking mechanism. The Internal locking mechanism prevents lateral movement or sliding of lead 1000 within tool 800 while the clinician positions tool 800 within the epidural space.

Implant tool 800 is then inserted through the proximal end of needle 900 as shown in FIG. 13 to access the epidural space. The clinician advances tool 800 within the epidural space of the patient (along path 1400 as shown in FIG. 14). The clinician may observe the advancement of marker 804 using fluoroscopy. The clinician continues advancement of tool 800 until the distal tip of tool 800 comes into contact with the medial aspect of the pedicle. When the distal tip of tool 800 contacts this defined structural landmark, the clinician receives tactile confirmation that the tool 800 is positioned correctly for deployment of lead 1000. In some embodiments, the distal end of tool 800 comprises compressible polymer material that is compressed by the clinician when it is placed into contact with the medial aspect of the pedicle by an appropriate amount of force. The inclusion of compressible material and/or deformable structure for the tip of tool 800 may enhance the ability of the clinician to feel to contact of tool 800 during the implant procedure.

When the distal tip of tool 800 is properly positioned, hub 802 is rotated back to the unlocked position. Lead 1000 is advanced through the tool 800 causing the distal tip of lead 1000 to exit side port 803. An interior surface of tool 800 near port 803 may be angled or curved to direct the distal tip of lead 1000 as it is advanced out of side port 803. Due to the position of the distal tip 800 and the use of side port 803, lead 1000 is positioned to proceed through the foramen as shown in FIG. 15 for positioning adjacent to the DRG to be stimulated. The advancement of the lead continues until the electrodes of the leads are suitably positioned to stimulate the DRG.

Electrode placement within the DRG may be confirmed using neurodiagnostic testing techniques such as somatosensory evoked potential (SSEP) and electromyography (EMG) adapted for the methods and systems described herein. One illustrative example includes the placement of sensing electrodes in the sensory nervous system above and below the DRG level having the implanted electrode(s). Test stimulation is applied to the DRG using one or more electrodes of the lead and the voltage potential at the sensory (SSEP or EMG) electrodes is measured above and below the targeted DRG to confirm that the electrodes of lead are implanted adjacent to the targeted DRG. The test stimulation may range from 0.4 v to 0.8v at 50 Hz to evoke the physiological response for measurement by the sensory electrodes.

Once the electrodes are properly positioned, one or more undulations may be created in the lead body within the epidural space to stabilize the lead's position as shown in FIG. 16. The creation of the undulations or "S-curve" configuration may occur by a combination of pulling and twisting tool 800 while pushing and/or pulling the lead and/or stylet. Additional details regarding creation of lead stabilizing shape are discussed in U.S. Patent Application Publication No. United States Application US20110276056, which is incorporated herein by reference.

Once the lead is implanted with its electrodes to stimulate the target DRG, the lead is connected to an implantable pulse generator (IPG) directly or indirectly using an "extension" connector. The IPG is programmed to generate electrical pulses according to a suitable neurostimulation program and the pulses are applied to the DRG using one or more electrodes of the implanted lead.

FIG. 18 depicts a neurostimulation system that may be employed according to some embodiments. Stimulation system 1800 generates electrical pulses for application to tissue of a patient, or subject, according to one embodiment. Stimulation system 1800 includes an implantable pulse generator (IPG) 850 that is adapted to generate electrical pulses for application to tissue of a patient. Implantable pulse generator 1850 typically includes a metallic housing that encloses a controller 1851, pulse generating circuitry 1852, a battery 1853, far-field and/or near field communication circuitry 1854, and other appropriate circuitry and components of the device. Controller 1851 typically includes a microcontroller or other suitable processor for controlling the various other components of the device. Software code is typically stored in memory of implantable pulse generator 1850 for execution by the microcontroller or processor to control the various components of the device (e.g., code to implement operations discussed herein). The software code stored in memory of pulse generator 1850 may support operations of embodiments disclosed herein. Communication circuitry 1854 may include far field and/or near field communication circuitry. In some embodiments, circuitry 1854 includes low energy BLUETOOTH™ communication circuitry.

Implantable pulse generator 1850 may comprise one or more attached extension components 1870 or be connected to one or more separate extension components 1870. Alternatively, one or more stimulation leads 1810 may be connected directly to implantable pulse generator 1850. Within Implantable pulse generator 1850, electrical pulses are generated by pulse generating circuitry 1852 and are provided to switching circuitry. The switching circuit connects to output wires, traces, lines, or the like (not shown) which are, in turn, electrically coupled to internal conductive wires (not shown) of a lead body 1872 of extension component 1870. The conductive wires, in turn, are electrically coupled to electrical connectors (e.g., "Bal-Seal" connectors) within connector portion 1871 of extension component 1870. The terminals of one or more stimulation leads 1810 are inserted within connector portion 1871 for electrical connection with respective connectors. Thereby, the pulses originating from implantable pulse generator 1850 and conducted through the conductors of lead body 1872 are provided to stimulation lead 1810. The pulses are then conducted through the conductors of stimulation lead 1810 and applied to tissue of a patient via electrodes 1811. Any suitable known or later developed design may be employed for connector portion 1871.

For implementation of the components within implantable pulse generator 1850, a processor and associated charge control circuitry for an implantable pulse generator is described in U.S. Pat. No. 7,571,007, entitled "SYSTEMS AND METHODS FOR USE IN PULSE GENERATION," which is incorporated herein by reference. Circuitry for recharging a rechargeable battery of an implantable pulse generator using inductive coupling and external charging circuits are described in U.S. Pat. No. 7,212,110, entitled "IMPLANTABLE DEVICE AND SYSTEM FOR WIRELESS COMMUNICATION," which is incorporated herein by reference.

An example and discussion of "constant current" pulse generating circuitry is provided in U.S. Patent Publication No. 2006/0170486 entitled "PULSE GENERATOR HAVING AN EFFICIENT FRACTIONAL VOLTAGE CONVERTER AND METHOD OF USE," which is incorporated herein by reference. One or multiple sets of such circuitry may be provided within implantable pulse generator 1850. Different pulses on different electrodes may be generated using a single set of pulse generating circuitry using consecutively generated pulses according to a "multi-stimset program" as is known in the art. Alternatively, multiple sets of such circuitry may be employed to provide pulse patterns that include simultaneously generated and delivered stimulation pulses through various electrodes of one or more stimulation leads as is also known in the art. Various sets of parameters may define the pulse characteristics and pulse timing for the pulses applied to various electrodes as is known in the art. Although constant current pulse generating circuitry is contemplated for some embodiments, any other suitable type of pulse generating circuitry may be employed such as constant voltage pulse generating circuitry.

Stimulation lead(s) 1810 may include a lead body of insulative material about a plurality of conductors within the material that extend from a proximal end of stimulation lead 1810 to its distal end. The conductors electrically couple a plurality of electrodes 1811 to a plurality of terminals (not shown) of stimulation lead 1810. The terminals are adapted to receive electrical pulses and the electrodes 1811 are adapted to apply stimulation pulses to tissue of the patient. Also, sensing of physiological signals may occur through electrodes 1811, the conductors, and the terminals. Additionally, or alternatively, various sensors (not shown) may be located near the distal end of stimulation lead 1810 and electrically coupled to terminals through conductors within the lead body 1872. Stimulation lead 1810 may include any suitable number of electrodes 1811, terminals, and internal conductors. Commercially available stimulation leads include the SlimTip™ DRG lead (Abbott, Plano Tex.).

Controller device 1860 (shown in FIG. 18) may be implemented to recharge battery 1853 of implantable pulse generator 1850 (although a separate recharging device could alternatively be employed). A "wand" 1865 may be electrically connected to controller device 1860 through suitable electrical connectors (not shown). The electrical connectors are electrically connected to a "primary" coil 1866 at the distal end of wand 1865 through respective wires (not shown). Typically, primary coil 1866 is connected to the wires through capacitors (not shown). Also, in some embodiments, wand 1865 may comprise one or more temperature sensors for use during charging operations.

The patient then places the primary coil 1866 against the patient's body immediately above the secondary coil (not shown), i.e., the coil of the implantable medical device. Preferably, the primary coil 1866 and the secondary coil are aligned in a coaxial manner by the patient for efficiency of the coupling between the primary and secondary coils. Controller device 1860 generates an AC-signal to drive current through primary coil 1866 of wand 1865. Assuming that primary coil 1866 and secondary coil are suitably positioned relative to each other, the secondary coil is disposed within the field generated by the current driven through primary coil 1866. Current is then induced in secondary coil. The current induced in the coil of the implantable pulse generator is rectified and regulated to recharge battery of implantable pulse generator 1850. The charging circuitry may also communicate status messages to controller device 1860 during charging operations using pulse-loading or any other suitable technique. For example, controller device 1860 may communicate the coupling status, charging status, charge completion status, etc.

External controller device 1860 is also a device that permits the operations of implantable pulse generator 1850 to be controlled by user after implantable pulse generator 1850 is implanted within a patient, although in alternative embodiments separate devices are employed for charging and programming. Also, multiple controller devices may be provided for different types of users (e.g., the patient or a clinician). Controller device 1860 can be implemented by utilizing a suitable handheld processor-based system that possesses wireless communication capabilities. Software is typically stored in memory of controller device 1860 to control the various operations of controller device 1860 (e.g., code to implement operations discussed herein). The software code stored in memory of device 1860 may support the operations according to embodiments disclosed herein. Also, the wireless communication functionality of controller device 1860 can be integrated within the handheld device package or provided as a separate attachable device. The user interface functionality of controller device 1860 is implemented using suitable software code for interacting with the user and using the wireless communication capabilities to conduct communications with implantable pulse generator 1850.

Controller device 1860 preferably provides one or more user interfaces to allow the user to operate implantable pulse generator 1850 according to one or more stimulation programs to treat the patient's disorder(s). Each stimulation program may include one or more sets of stimulation parameters including pulse amplitude, pulse width, pulse frequency or inter-pulse period, pulse repetition parameter (e.g., number of times for a given pulse to be repeated for respective stimset during execution of program), etc. Implantable pulse generator 1850 modifies its Internal parameters in response to the control signals from controller device 1860 to vary the stimulation characteristics of stimulation pulses transmitted through stimulation lead 1810 to the tissue of the patient. Neurostimulation systems, stimsets, and multi-stimset programs are discussed in PCT Publication No. WO 2001/93953, entitled "NEUROMODULATION THERAPY SYSTEM," and U.S. Pat. No. 7,228,179, entitled "METHOD AND APPARATUS FOR PROVIDING COMPLEX TISSUE STIMULATION PATTERNS," which are incorporated herein by reference.

Pulse generator device 1850 and controller device 1860 may be adapted to apply different types of neurostimulation. One or more stimulation sets or programs may be defined with tonic stimulation. Also, these devices may support burst stimulation as disclosed in U.S. Pat. No. 8,934,981 which is incorporated herein by reference. In burst stimulation, groups of pulses are provided at a relatively high frequency (greater than 250 Hz) with adjacent groups of pulses separated by a quiet period. The groups are repeated at a relatively lower frequency (e.g., 40 Hz or other physiologically relevant frequencies). These devices may support "noise" stimulation such as described in U.S. Pat. No. 9,498,634, which is incorporated herein by references. These devices may also support high frequency stimulation (e.g., 1500 Hz-20,000 Hz).

Example commercially available neurostimulation systems include the PROTEGE™, PRODIGY™, PROCLAIM™, INFINITY™, AXIUM™ pulse generators and CLINICIAN PROGRAMMER APP from Abbott Laboratories.

It Is to be understood that the above description Is intended to be illustrative, and not restrictive. For example, the above-described embodiments (and/or aspects thereof) may be used in combination with each other. In addition, many modifications may be made to adapt a particular situation or material to the teachings of the invention without departing from its scope. While the dimensions, types of materials and coatings described herein are intended to define the parameters of the invention, they are by no means limiting and are exemplary embodiments. Many other embodiments will be apparent to those of skill in the art upon reviewing the above description. The scope of the invention should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means-plus-function format and are not intended to be Interpreted based on 45 U.S.C. § 112(f), unless and until such claim limitations expressly use the phrase "means for" followed by a statement of function void of further structure. and processes included within the hardware modules.

The invention claimed is:

1. A method of implanting a stimulation lead to stimulate a root ganglion (DRG) of a patient, comprising:
placing a distal portion of the stimulation lead within an implant tool;
accessing the epidural space of the patient with a distal end of the implant tool;
contacting a surface of a pedicle of the patient with a closed distal tip of the implant tool above a foramen leading to a target DRG;

in response to contacting the surface of the pedicle with the closed distal tip, advancing the stimulation lead from a side port of the implant tool, wherein the side port is located proximal to the closed distal tip of the implant tool;

advancing the stimulation lead through the foramen to position one or more electrodes of the stimulation lead adjacent to the target DRG; and providing electrical stimulation to the target DRG to stimulate the target DRG using one or more electrodes of the stimulation lead.

2. The method of claim 1 wherein the accessing the epidural space comprises: advancing a distal end of the implant tool through an epidural needle.

3. The method of claim 1 further comprising:
applying fluoroscopy to observe a radiopaque marker on a distal end of the implant tool while manipulating the distal end of the implant tool within the epidural space of the patient.

4. The method of claim 1 wherein the surface of the pedicle is located on a medial aspect of the pedicle.

5. The method of claim 1 wherein the implant tool comprises a curved or angled interior surface near the side port to cause the stimulation lead to curve as it is advanced out of the side port of the implant tool.

6. The method of claim 1 further comprising:
locking the stimulation lead in place within the implant tool before advancing accessing the epidural space of the patient with the implant tool.

7. The method of claim 6 wherein the locking comprises twisting a hub on a proximal end of the implant tool to lock the stimulation lead in place.

8. The method of claim 1 further comprising:
forming one or more undulations in the stimulation lead within the epidural space of the patient to stabilize the stimulation lead after implant.

9. The method of claim 1 further comprising:
connecting the stimulation lead to an implantable pulse generator.

10. A method of implanting a stimulation lead to stimulate a dorsal root ganglion (DRG) of a patient, comprising:
placing a distal portion of the stimulation lead within an implant tool;
adjusting a distance between a closed distal tip of the implant tool and a side port of the implant tool, wherein the side port is located proximal to the closed distal tip of the implant tool;
accessing the epidural space of the patient with a distal end of the implant tool;
contacting a surface of a pedicle of the patient with the closed distal tip of the implant tool above a foramen leading to a target DRG;
in response to contacting the surface of the pedicle with the closed distal tip, advancing the stimulation lead from the side port of the implant tool;
advancing the stimulation lead through the foramen to position one or more electrodes of the stimulation lead adjacent to the target DRG; and
providing electrical stimulation to the target DRG to stimulate the target DRG using one or more electrodes of the stimulation lead.

11. The method of claim 10 wherein the accessing the epidural space comprises: advancing a distal end of the implant tool through an epidural needle.

12. The method of claim 10 further comprising:
applying fluoroscopy to observe a radiopaque marker on a distal end of the implant tool while manipulating the distal end of the implant tool within the epidural space of the patient.

13. The method of claim 10 wherein the surface of the pedicle is located on a medial aspect of the pedicle.

14. The method of claim 10 wherein the implant tool comprises a curved or angled interior surface near the side port to cause the stimulation lead to curve as it is advanced out of the side port of the implant tool.

15. The method of claim 10 further comprising:
locking the stimulation lead in place within the implant tool before advancing accessing the epidural space of the patient with the implant tool.

16. The method of claim 15 wherein the locking comprises twisting a hub on a proximal end of the implant tool to lock the stimulation lead in place.

17. The method of claim 10 further comprising:
forming one or more undulations in the stimulation lead within the epidural space of the patient to stabilize the stimulation lead after implant.

18. The method of claim 10 further comprising:
connecting the stimulation lead to an implantable pulse generator.

19. The method of claim 10 further comprising manipulating a portion of the closed distal tip of the implant tool, wherein adjustment of the distance between the closed distal tip of the implant tool and the side port of the implant tool is based on the manipulating.

20. The method of claim 19 wherein the manipulating comprises twisting the portion of the closed distal tip or sliding the portion of the closed distal tip.

* * * * *

UNITED STATES PATENT AND TRADEMARK OFFICE
CERTIFICATE OF CORRECTION

PATENT NO. : 11,612,412 B2
APPLICATION NO. : 16/389291
DATED : March 28, 2023
INVENTOR(S) : Matthew K. Dion et al.

It is certified that error appears in the above-identified patent and that said Letters Patent is hereby corrected as shown below:

In the Specification

At Column 1, Line number 24, delete "Internal" and replace with --internal--.
At Column 2, Line number 33, delete "Illustrates" and replace with --illustrates--.
At Column 2, Line number 36, delete "Invention" and replace with --invention--.
At Column 2, Line number 49, delete "Illustrates" and replace with --illustrates--.
At Column 3, Line number 21, delete "Into" and replace with --into--.
At Column 3, Line number 39, delete "Implanted" and replace with --implanted--.
At Column 3, Line number 66, delete "Is" and replace with --is--.
At Column 4, Line number 56, delete "Invention" and replace with --invention--.
At Column 4, Line number 63, delete "Illustrated" and replace with --illustrated--.
At Column 5, Line number 33, delete "Influenced" and replace with --influenced--.
At Column 7, Line number 16, delete "Illustrated" and replace with --illustrated--.
At Column 7, Line number 23, delete "Is" and replace with --is--.
At Column 8, Line number 41, delete "Internal" and replace with --internal--.
At Column 9, Line number 67, delete "Implantable" and replace with --implantable--.
At Column 11, Line number 67, delete "Internal" and replace with --internal--.
At Column 12, Line number 31, delete both occurrences of "Is" and replace with --is--.
At Column 12, Line number 53, delete "Interpreted" and replace with --interpreted--.

In the Claims

At Column 12, Claim number 1, Line number 60, delete "a root ganglion (DRG)" and replace with --a dorsal root ganglion (DRG)--.

Signed and Sealed this
Twenty-third Day of May, 2023

Katherine Kelly Vidal
*Director of the United States Patent and Trademark Office*